(12) United States Patent
Hikida et al.

(10) Patent No.: US 11,174,221 B2
(45) Date of Patent: Nov. 16, 2021

(54) AROMATIC AMINE COMPOUND, CURING AGENT FOR EPOXY COMPOUND, CURABLE COMPOSITION, CURED PRODUCT, METHOD FOR PRODUCING CURED PRODUCT, AND METHOD FOR PRODUCING AROMATIC AMINE COMPOUND

(71) Applicant: TOKYO OHKA KOGYO CO., LTD., Kawasaki (JP)

(72) Inventors: Jiro Hikida, Kawasaki (JP); Dai Shiota, Kawasaki (JP)

(73) Assignee: Tokyo Ohka Kogyo Co., Ltd., Kawasaki (JP)

( * ) Notice: Subject to any disclaimer, the term of this patent is extended or adjusted under 35 U.S.C. 154(b) by 0 days.

(21) Appl. No.: 16/633,466

(22) PCT Filed: Jul. 26, 2018

(86) PCT No.: PCT/JP2018/028132
§ 371 (c)(1),
(2) Date: Jan. 23, 2020

(87) PCT Pub. No.: WO2019/022203
PCT Pub. Date: Jan. 31, 2019

(65) Prior Publication Data
US 2021/0130284 A1    May 6, 2021

(30) Foreign Application Priority Data
Jul. 27, 2017    (JP) .............................. JP2017-145639

(51) Int. Cl.
| | | |
|---|---|---|
| *C07C 231/02* | (2006.01) | |
| *C07C 231/12* | (2006.01) | |
| *C07C 237/40* | (2006.01) | |
| *C08G 59/50* | (2006.01) | |

(52) U.S. Cl.
CPC .......... *C07C 231/02* (2013.01); *C07C 231/12* (2013.01); *C08G 59/5033* (2013.01); *C07C 237/40* (2013.01); *C07C 2603/18* (2017.05)

(58) Field of Classification Search
None
See application file for complete search history.

(56) References Cited

U.S. PATENT DOCUMENTS

| | | |
|---|---|---|
| 4,684,678 A | 8/1987 | Gene et al. |
| 2007/0255075 A1 | 11/2007 | Mori |
| 2016/0222165 A1 | 8/2016 | Wakita et al. |

FOREIGN PATENT DOCUMENTS

| | | |
|---|---|---|
| CN | 102617382 A | 8/2012 |
| JP | H06-039520 A | 2/1994 |
| JP | S61-283617 A | 5/1994 |
| JP | 2006-219396 A | 8/2006 |
| JP | H10-298150 A | 8/2006 |
| JP | 2009062398     * | 3/2009 |
| JP | 2010-180349 A | 4/2010 |
| JP | 5773090 B1 | 2/2015 |
| JP | 2015-054825 A | 3/2015 |

OTHER PUBLICATIONS

He, X. et al., European Polymer Journal, 2013,vol. 49, pp. 2759-2768.
San-Jose, N.et al., European Polymer Journal, 2008, vol. 44,pp. 3578-3587.
Zhang, L. et al., Journal of Macromolecular Science, Part A: Pure and Applied Chemistry, 2016, vol. 53, No. 2, p. 88-95.

* cited by examiner

*Primary Examiner* — Amy C Bonaparte
(74) *Attorney, Agent, or Firm* — Knobbe Martens Olson & Bear LLP

(57) ABSTRACT

An aromatic amine compound capable of satisfactorily forming a cured product having exceptional alkali resistance by reaction with an epoxy compound; a curing agent for an epoxy compound, the curing agent including the aromatic amine compound; a curable composition including the curing agent for an epoxy compound; a cured product of the curable composition; a method for producing the cured product; and a method for producing the abovementioned aromatic amine compound. The aromatic amine compound has a structure such that a specific position in a central skeleton comprising a fused ring such as a fluorene ring is substituted with a side-chain group including two aromatic groups linked by a flexible bond such as an amide bond, at least one amino group is bonded to the end of the side-chain group, and the structure has no hydroxyl groups.

15 Claims, No Drawings

AROMATIC AMINE COMPOUND, CURING AGENT FOR EPOXY COMPOUND, CURABLE COMPOSITION, CURED PRODUCT, METHOD FOR PRODUCING CURED PRODUCT, AND METHOD FOR PRODUCING AROMATIC AMINE COMPOUND

This application is the U.S. National Phase under 35 U.S.C. § 371 of International Application PCT/JP2018/028132, filed Jul. 26, 2018, designating the U.S., and published in Japanese as WO 2019/022203 on Jan. 31, 2019, which claims priority to Japanese Patent Application No. 2017-145639, filed Jul. 27, 2017, the entire content of which is incorporated herein by reference.

TECHNICAL FIELD

The present invention relates to an aromatic amine compound, a curing agent for an epoxy compound, a curable composition, a cured product, a method for producing a cured product, and a method for producing an aromatic amine compound.

BACKGROUND ART

An aromatic amine compound is used for various applications such as curing agents of curable compositions. For example, curable compositions including epoxy compounds and aromatic amine compounds are widely used in applications such as adhesives, electronic component sealing, and matrix formation of fiber reinforced composite materials, and the like.

For example, Patent Document 1 discloses a curable composition including an epoxy compound having an epoxy group in a molecule and an aromatic amine compound. Furthermore, Patent Document 2 discloses an aromatic amine compound that can be used as a precursor of polyimide resin.

Patent Document 1: Japanese Examined Patent Application Publication No. H06-39520
Patent Document 2: Japanese Patent No. 5773090

DISCLOSURE OF THE INVENTION

Problems to be Solved by the Invention

A structure of an aromatic amine compound is optimized according to the applications. For example, when the aromatic amine compound is used as a curing agent of an epoxy compound, in order to mitigate the hardness or the brittleness of the cured product, it is preferable in the aromatic amine compound that rigid rings such as an aromatic ring are linked by flexible divalent groups such as amide bonds (—CONH—) and ester bonds (—COO—).

Patent Document 2 describes an aromatic amine compound (formula (21)) in which an aromatic ring and a fluorene ring are linked to each other by an amide bond (—CONH—). However, when epoxy compound is cured using the aromatic amine compound described in the formula (21) in Patent Document 2, the resultant cured product does not necessarily have good alkali resistance.

The present invention has been made in view of the above problem, and an object of the present invention is to provide an aromatic amine compound capable of satisfactorily forming a cured product having excellent alkali resistance by reaction with an epoxy compound; a curing agent for an epoxy compound, the curing agent including the aromatic amine compound; a curable composition including the curing agent for an epoxy compound; a cured product of the curable composition; a method for producing the cured product; and a method for producing the abovementioned aromatic amine compound.

Means for Solving the Problems

The present inventors have found that the above problem can be solved when the aromatic amine compound has a structure such that a specific position in a central skeleton including a fused ring such as a fluorene ring is substituted by a side-chain group including two aromatic groups linked by a flexible bond such as an amide bond, at least one amino group is bonded to the terminal of the side-chain group, and the structure has no hydroxyl groups, and have completed the present invention. Specifically, the present invention provides the following.

A first aspect of the present invention is an aromatic amine compound represented by the following formula (a1):

[Chem. 1]

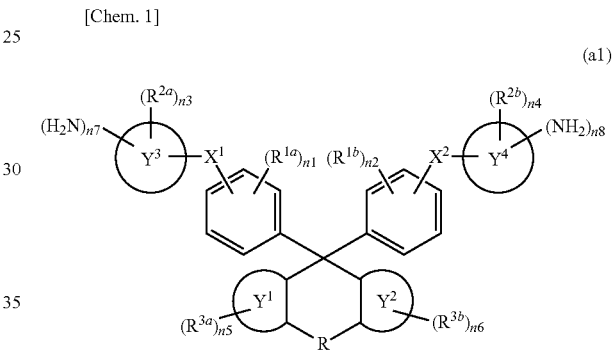

(a1)

wherein in the formula (a1), $R^{1a}$, $R^{1b}$, $R^{2a}$, $R^{2b}$, $R^{3a}$, and $R^{3b}$ are each independently a monovalent hydrocarbon group, a group represented by —$OR^{4a}$, a group represented by —$SR^{4b}$, an acyl group, an alkoxycarbonyl group, a halogen atom, a cyano group, a group represented by —$NHR^{4c}$, or a group represented by —$N(R^{4d})_2$, wherein the monovalent hydrocarbon group, the group represented by —$OR^{4a}$, the group represented by —$SR^{4b}$, and the acyl group, the alkoxycarbonyl group, the group represented by —$NHR^{4c}$, and a group represented by —$N(R^{4d})_2$ may be substituted by one or more groups selected from the group consisting of a group represented by —$OR^{4e}$, a group represented by —$SR^{4f}$, an acyl group, an alkoxycarbonyl group, a halogen atom, a cyano group, a group represented by —$NHR^{4g}$, and a group represented by —$N(R^{4h})_2$;
$R^{4a}$ to $R^{4g}$ are each independently a monovalent hydrocarbon group;
$X^1$ and $X^2$ are each independently —CO—NH—, —CO—O—, —NH—CO—NH—, —CO—NH—CO—, —O—CO—NH—, or —CO—NH—CO—NH—;
a ring $Y^1$, a ring $Y^2$, a ring $Y^3$, and a ring $Y^4$ each independently represent an aromatic hydrocarbon ring;
R is a single bond, a methylene group which may have a substituent, an ethylene group which may have a substituent and including a heteroatom between two carbon atoms, a group represented by —O—, a group represented by —NH—, or a group represented by —S—;
n1 and n2 are each independently an integer of 0 or more and 4 or less;

n3 and n4 are each independently an integer of 0 or more and 5 or less;

n5 and n6 are each independently an integer of 0 or more and 4 or less;

n7 and n8 are each independently an integer of 0 or more and 2 or less;

n3+n7 and n4+n8 are each independently an integer of 0 or more and 5 or less; and n7+n8 is an integer of 1 or more and 4 or less.

A second aspect of the present invention is a curing agent for an epoxy compound, including the aromatic amine compound according to the first aspect.

A third aspect of the present invention is a curable composition including an (A) epoxy compound and a (B) curing agent, wherein the (B) curing agent is the curing agent for an epoxy compound according to the second aspect.

A fourth aspect of the present invention is a cured product of the curable composition of the third aspect.

A fifth aspect of the present invention is a method for producing a cured product, the method including:

molding the curable composition according to the third aspect into a predetermined shape; and heating the molded curable composition.

A sixth aspect of the present invention is a method for producing an aromatic amine compound according to the first aspect, the method including hydrogenating a nitro group of an aromatic nitro compound represented by the following formula (a1-1):

[Chem. 2]

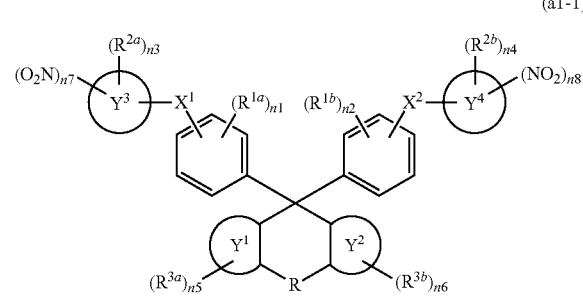

(a1-1)

(wherein, in the formula (a1-1), $R^{1a}$, $R^{1b}$, $R^{2a}$, $R^{2b}$, $R^{3a}$, $R^{3b}$, $X^1$, $X^2$, a ring $Y^1$, a ring $Y^2$, a ring $Y^3$, a ring $Y^4$, R, and n1 to n8 are the same as those in the formula (a1))

to be converted into an amino group.

A seventh aspect of the present invention is a method for producing an aromatic amine compound according to the first aspect, the method including:

deprotecting an amino group that is protected by $Z^1$—NH— or $Z^2$—NH— of the aromatic compound represented by the following formula (a1-2):

[Chem. 3]

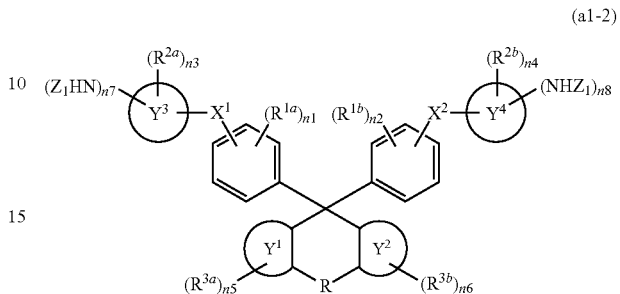

(a1-2)

(wherein, in the formula (a1-2), $R^{1a}$, $R^{1b}$, $R^{2a}$, $R^{2b}$, $R^{3a}$, $R^{3b}$, $X^1$, $X^2$, a ring $Y^1$, a ring $Y^2$, a ring $Y^3$, a ring $Y^4$, R, and n1 to n8 are the same as those in the formula (a1), $Z^1$ and $Z^2$ are each independently a protecting group capable of protecting and deprotecting an amino group).

An eighth aspect of the present invention is a method for producing an aromatic amine compound according to the first aspect, the method including reacting an aromatic compound represented by the following formula (a1-1a), a compound represented by the following formula (a1-3b), and a compound represented by the following formula (a1-3c):

[Chem. 4]

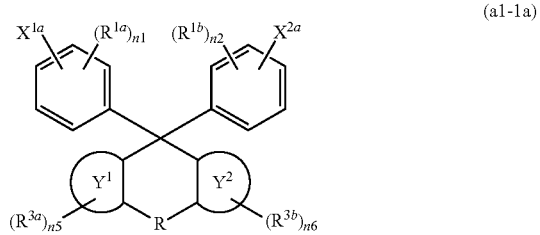

(a1-1a)

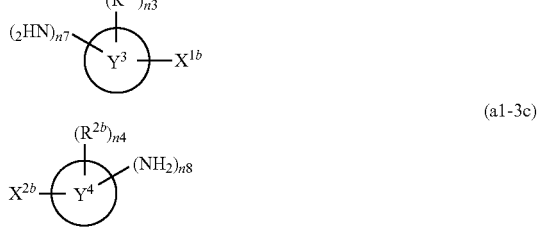

(a1-3b)

(a1-3c)

wherein, in the formulae (a1-1a), (a1-3b), and (a1-3c), $R^{1a}$, $R^{1b}$, $R^{2a}$, $R^{2b}$, $R^{3a}$, $R^{3b}$, a ring $Y^1$, a ring $Y^2$, a ring $Y^3$, a ring $Y^4$, R, and n1 to n8 are the same as those in the formula (a1), a group $X^{1a}$ is a group that forms a group $X^1$ in the formula (a1) by a reaction with a group $X^{1b}$, and a group $X^{2a}$ is a group that forms a group $X^2$ in the formula (a1) by a reaction with a group $X^{2b}$, to produce the aromatic amine compound represented by the formula (a1), wherein the reaction between the group $X^{1a}$ and the group $X^{1b}$ generates the group $X^1$, and the reaction between the group $X^{2a}$ and the group $X^{2b}$ generates the group $X^2$;

wherein a combination of the group $X^{1a}$ and the group $X^{2b}$ and a combination of the group $X^{2a}$ and the group $X^{2b}$ are each independently
a combination of a carboxy group (—COOH) or a halocarbonyl group (—COHal) and an amino group (—NH$_2$),
a combination of a carboxy group (—COOH) or a halocarbonyl group (—COHal), and a hydroxyl group, or
a combination of a carboxy group (—COOH) or a halocarbonyl group (—COHal) and a carbamoyl group (—CO—NH$_2$).

Effects of the Invention

The present invention can provide an aromatic amine compound capable of satisfactorily forming a cured product having excellent alkali resistance by reaction with an epoxy compound; a curing agent for an epoxy compound, the curing agent including the aromatic amine compound; a curable composition including the curing agent for an epoxy compound; a cured product of the curable composition; a method for producing the cured product; and a method for producing the above-mentioned aromatic amine compound.

PREFERRED MODE FOR CARRYING OUT THE INVENTION

<<Aromatic Amine Compound>>

An aromatic amine compound is an aromatic amine compound represented by the following formula (a1):

[Chem. 5]

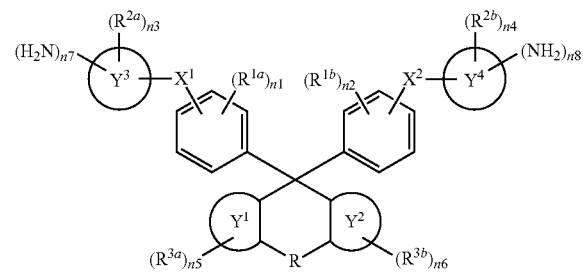

(a1)

(wherein, in the formula (a1), $R^{1a}$, $R^{1b}$, $R^{2a}$, $R^{2b}$, $R^{3a}$, and $R^{3b}$ are each independently a monovalent hydrocarbon group, a group represented by —OR$^{4a}$, a group represented by —SR$^{4b}$, an acyl group, an alkoxycarbonyl group, a halogen atom, a cyano group, a group represented by —NHR$^{4c}$, or a group represented by —N(R$^{4d}$)$_2$, wherein the monovalent hydrocarbon group, the group represented by —OR$^{4a}$, the group represented by —SR$^{4b}$, and the acyl group, the alkoxycarbonyl group, the group represented by —NHR$^{4c}$, and a group represented by —N(R$^{4d}$)$_2$ may be substituted by one or more groups selected from the group consisting of a group represented by —OR$^{4e}$, a group represented by —SR$^{4f}$, an acyl group, an alkoxycarbonyl group, a halogen atom, a cyano group, a group represented by —NHR$^{4g}$, and a group represented by —N(R$^{4h}$)$_2$;
$R^{4a}$ to $R^{4g}$ are each independently a monovalent hydrocarbon group;
$X^1$ and $X^2$ are each independently —CO—NH—, —CO—O—, —NH—CO—NH—, —CO—NH—CO—, —O—CO—NH—, or —CO—NH—CO—NH—;

a ring $Y^1$, a ring $Y^2$, a ring $Y^3$, and a ring $Y^4$ each independently represent an aromatic hydrocarbon ring;
R is a single bond, a methylene group which may have a substituent, an ethylene group which may have a substituent and including a heteroatom between two carbon atoms, a group represented by —O—, a group represented by —NH—, or a group represented by —S—;
n1 and n2 are each independently an integer of 0 or more and 4 or less;
n3 and n4 are each independently an integer of 0 or more and 5 or less;
n5 and n6 are each independently an integer of 0 or more and 4 or less;
n1 and n8 are each independently an integer of 0 or more and 2 or less;
n3+n7 and n4+n8 are each independently an integer of 0 or more and 5 or less; and
n7+n8 is an integer of 1 or more and 4 or less.

The application of use of the aromatic amine compound is not particularly limited. The aromatic amine compound is suitably used as a curing agent for an epoxy compound. The aromatic amine compound represented by the formula (a1) does not include an alkali soluble group such as a carboxy group and a phenolic hydroxyl group in the structure. Therefore, when an epoxy compound is cured by using the aromatic amine compound represented by the formula (a1), a cured product having excellent alkali resistance can be formed. Furthermore, the aromatic amine compound can be used for various applications in which aromatic amine compounds have conventionally been used. For example, when the aromatic amine compound has two or more amino groups, it can be used as a monomer for synthesis of a polyamide resin. Furthermore, the aromatic amine compound can be suitably used as a raw material of diazonium salt or tetrazonium salt for synthesis of azo dye.

In the above formula (a1), examples of the ring $Y^1$, the ring $Y^2$, the ring $Y^3$, and the ring $Y^4$ include a benzene ring and fused polycyclic aromatic hydrocarbon rings [for example, fused di- to tetracyclic aromatic hydrocarbon rings such as fused dicyclic hydrocarbon rings (for example, $C_{8-20}$ fused dicyclic hydrocarbon rings, preferably $C_{10-16}$ fused dicyclic hydrocarbon rings, such as naphthalene ring) and fused tricyclic aromatic hydrocarbon rings (for example, anthracene ring or phenanthrene ring)]. The ring $Y^1$, the ring $Y^2$, the ring $Y^3$, and the ring $Y^4$ are preferably a benzene ring or a naphthalene ring, and more preferably a benzene ring. The ring $Y^3$ and the ring $Y^4$ may be the same as or different from each other, and particularly preferably, the both rings are a benzene ring. The ring $Y^1$ and the ring $Y^2$ may be the same as or different from each other, and particularly preferably, the both rings are a benzene ring.

In the formula (a1), $X^1$ and $X^2$ are —CO—NH—, —CO—O—, —NH—CO—NH—, —CO—NH—CO—, —O—CO—NH—, or —CO—NH—CO—NH—. The direction of the bond of them is not particularly limited. For example, when $X^1$ is —CO—NH—, the ring $Y^3$ side may be a carbonyl group (—CO—) or an amino group (—NH—).

In the formula (a1), as $R^{1a}$, $R^{1b}$, $R^{2a}$, $R^{2b}$, $R^{3a}$, and $R^{3b}$, a non-reactive substituent is preferable. Examples of the non-reactive substituent include monovalent hydrocarbon group such as alkyl groups (for example, $C_{1-12}$ alkyl groups such as methyl, ethyl, propyl, isopropyl, and butyl groups, preferably $C_{1-8}$ alkyl groups, more preferably $C_{1-6}$ alkyl groups), cycloalkyl groups ($C_{5-10}$ cycloalkyl groups such as cyclohexyl group, preferably $C_{5-8}$ cycloalkyl groups, more preferably $C_{5-6}$ cycloalkyl groups), aryl groups (for example, $C_{6-14}$ aryl groups such as phenyl, tolyl, xylyl, and naphthyl groups, preferably $C_{6-10}$ aryl groups, more preferably $C_{6-8}$ aryl groups), and aralkyl groups ($C_{6-10}$ aryl $C_{1-4}$ alkyl groups such as benzyl and phenethyl groups);

groups represented by —$OR^{4a}$ such as alkoxy groups (for example, $C_{1-12}$ alkoxy groups such as methoxy, ethoxy, propoxy, and butoxy groups, preferably $C_{1-8}$ alkoxy groups, more preferably $C_{1-6}$ alkoxy groups), cycloalkoxy groups ($C_{5-10}$ cycloalkoxy groups such as cyclohexyloxy groups), aryloxy groups ($C_{6-10}$ aryloxy groups such as phenoxy group), and aralkyloxy groups (for example, $C_{6-10}$ aryl $C_{1-4}$ alkyloxy groups such as benzyloxy group);

groups represented by —$SR^{4b}$ such as alkylthio groups (for example, $C_{1-12}$ alkylthio groups such as methylthio, ethylthio, propylthio, and butylthio groups, preferably $C_{1-8}$ alkylthio groups, more preferably $C_{1-6}$ alkylthio groups), cycloalkylthio groups ($C_{5-10}$ cycloalkylthio groups such as a cyclohexylthio group), aryl thio groups ($C_{6-10}$ aryl thio groups such as a phenylthio group), and aralkyl thio groups (for example, $C_{6-10}$ aryl $C_{1-4}$ alkylthio groups such as a benzylthio group); acyl groups ($C_{1-6}$ acyl groups such as an acetyl group); alkoxycarbonyl groups ($C_{1-4}$ alkoxycarbonyl groups such as a methoxycarbonyl group);

halogen atoms (for example, a fluorine atom, a chlorine atom, a bromine atom, and an iodine atom);

a cyano group;

groups represented by —$NHR^{4c}$ such as alkylamino groups ($C_{1-12}$ alkylamino groups such as a methylamino group, an ethylamino group, a propylamino group, and a butylamino group, preferably $C_{1-8}$ alkylamino groups, more preferably $C_{1-6}$ alkylamino groups), cycloalkylamino groups ($C_{5-10}$ cycloalkylamino groups such as a cyclohexylamino group), arylamino groups ($C_{6-10}$ aryl amino groups such as a phenylamino group), and aralkyl amino groups (for example, $C_{6-10}$ aryl $C_{1-4}$ alkylamino groups such as a benzylamino group);

groups represented by —$N(R^{4d})_2$ such as dialkylamino groups (di($C_{1-12}$ alkyl)amino groups such as dimethylamino group, diethylamino group, dipropylamino group, and dibutylamino group, preferably di($C_{1-8}$ alkyl)amino groups, more preferably di($C_{1-6}$ alkyl)amino groups), dicycloalkylamino groups (di($C_{5-10}$ cycloalkyl)amino groups such as dicyclohexylamino group), diaryl amino groups (di($C_{6-10}$ aryl)amino groups such as diphenylamino group), and diaralkyl amino groups (for example, di($C_{6-10}$ aryl $C_{1-4}$ alkyl) amino groups such as dibenzylamino group).

When $R^{1a}$, $R^{1b}$, $R^{2a}$, $R^{2b}$, $R^{3a}$, and $R^{3b}$ are a monovalent hydrocarbon group, a group represented by —$OR^{4a}$, a group represented by —$SR^{4b}$, an acyl group, an alkoxycarbonyl group, a group represented by —$NHR^{4c}$, and a group represented by —$N(R^{4d})_2$, these groups may be substituted by one or more groups selected from the group consisting of a group represented by —$OR^{4e}$, a group represented by —$SR^{4f}$, an acyl group, an alkoxycarbonyl group, a halogen atom, a cyano group, a group represented by —$NHR^{4?}$, and a group represented by —$N(R^{4h})_2$.

Preferable examples of these substituent are the same as preferable examples of a group represented by —$OR^{4a}$, a group represented by —$SR^{4b}$, an acyl group, an alkoxycarbonyl group, a halogen atom, a cyano group, a group represented by —$NHR^{4c}$, and a group represented by —$N(R^{4d})_2$.

When a plurality of each of $R^{1a}$, $R^{1b}$, $R^{2a}$, $R^{2b}$, $R^{3a}$, and $R^{3b}$ is present, the plurality of groups may be the same as or different from each other. Substituted positions of $R^{1a}$, $R^{1b}$, $R^{2a}$, $R^{2b}$, $R^{3a}$, and $R^{3b}$ are not particularly limited.

In the formula (a1), n1 and n2 are each independently an integer of 0 or more and 4 or less, preferably 0 or 1, more preferably 0. n3 and n4 are each independently an integer of 0 or more and 5 or less, preferably 0 or 1, more preferably 0. n5 and n6 are each independently an integer of 0 or more and 5 or less, preferably 0 or 1, more preferably 0. n1 and n8 are each independently an integer of 0 or more and 2 or less, preferably 1.

In the formula (a1), R is a single bond, a methylene group which may have a substituent, an ethylene group which may have a substituent and including a heteroatom between two carbon atoms, a group represented by —O—, a group represented by —NH—, or a group represented by —S—, and typically a single bond. Examples of the substituents include a cyano group, a halogen atom (a fluorine atom, a chlorine atom, a bromine atom, and the like), a monovalent hydrocarbon group [for example, an alkyl group ($C_{1-6}$ alkyl groups such as a methyl group, an ethyl group, a propyl group, an isopropyl group, a butyl group, and a t-butyl group), an aryl group ($C_{6-10}$ aryl groups such as a phenyl group)], and the like. Examples of the hetero atom include an oxygen atom, a nitrogen atom, a sulfur atom, a silicon atom, and the like.

In the formula (a1), it is preferable that the ring $Y^1$ and the ring $Y^2$ are each a benzene ring, and R is a single bond. In other words, it is preferable that the aromatic amine compound represented by the formula (a1) includes a fluorene ring.

In the formula (a1), n3+n7 and n4+n8 are each independently an integer of 0 or more and 5 or less. n7 and n8 may be the same as or different from each other. n7+n8 is an integer of 1 or more and 4 or less. Accordingly, one or more amino groups are bonded to at least one of the ring $Y^3$ and the ring $Y^4$. n7+n8 is preferably 2 or 3, and more preferably 2. Particularly preferably, both n7 and n8 are 1.

As the aromatic amine compound represented by the formula (a1) described above, a compound represented by the following formula (a2):

[Chem. 6]

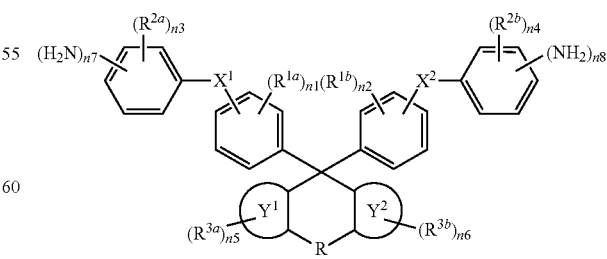

(a2)

(wherein, in the formula (a2), $R^{1a}$, $R^{1b}$, $R^{2a}$, $R^{2b}$, $R^{3a}$, $R^{3b}$, a ring $Y^1$, a ring $Y^2$, a ring $Y^3$, a ring $Y^4$, R, and n1 to n8 are the same as those in the formula (a1)) is preferable.

As the aromatic amine compound represented by the formula (a2), a compound represented by the following formula (a3):

[Chem. 7]

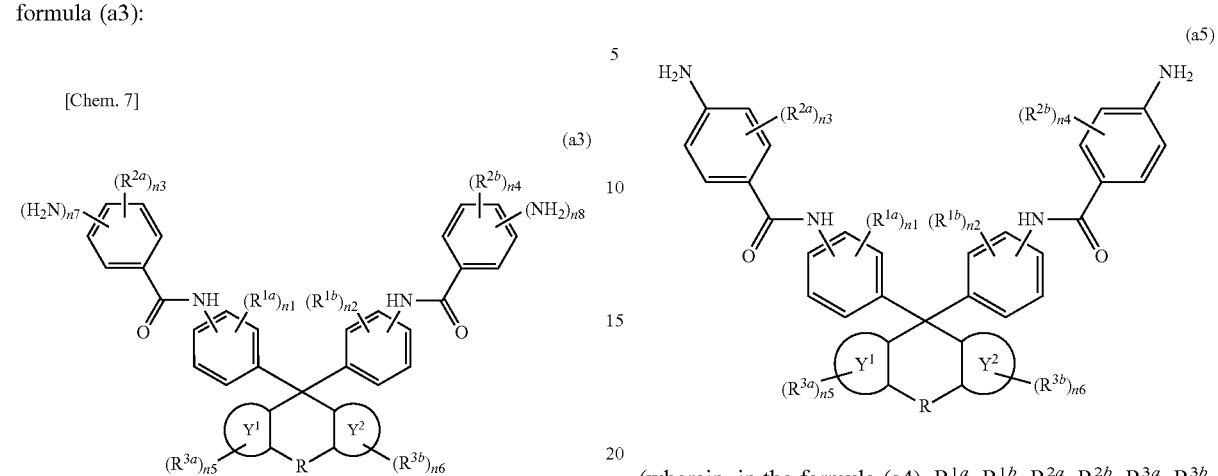

(a3)

(wherein, in the formula (a3), $R^{1a}$, $R^{1b}$, $R^{2a}$, $R^{2b}$, $R^{3a}$, $R^{3b}$, $X^1$, $X^2$, a ring $Y^1$, a ring $Y^2$, R, and n1 to n8 are the same as those in the formula (a1)) is preferable.

As the aromatic amine compound represented by the formula (a3), a compound represented by the following formula (a4):

[Chem. 8]

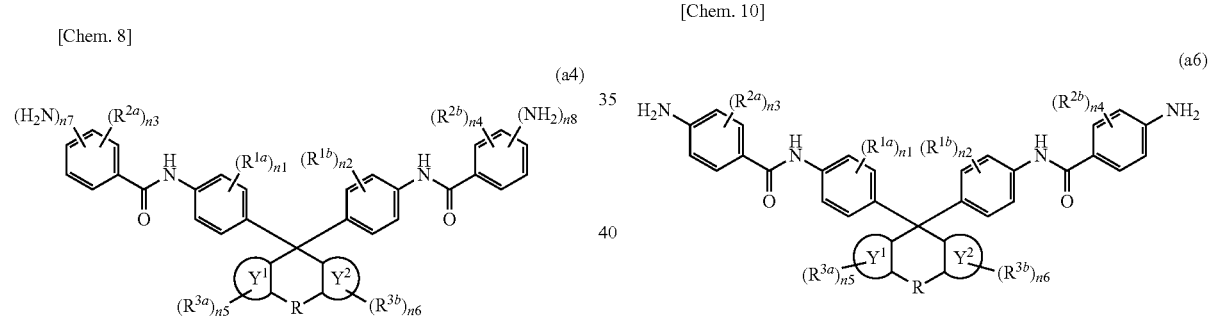

(a4)

(wherein, in the formula (a4), $R^{1a}$, $R^{1b}$, $R^{2a}$, $R^{2b}$, $R^{3a}$, $R^{3b}$, $X^1$, $X^2$, a ring $Y^1$, a ring $Y^2$, R, and n1 to n8 are the same as those in the formula (a1)) is preferable.

As the aromatic amine compound represented by the formula (a3), a compound represented by the following formula (a5):

[Chem. 9]

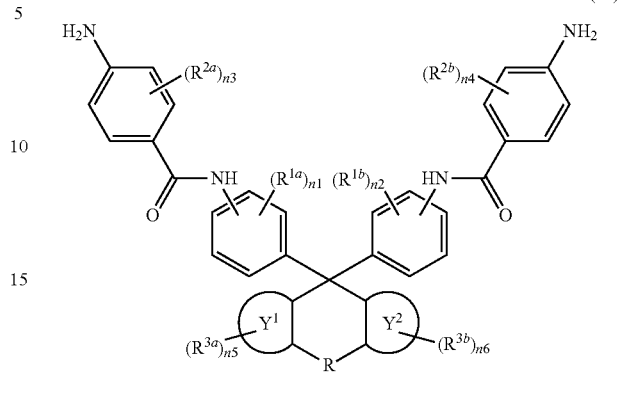

(a5)

(wherein, in the formula (a4), $R^{1a}$, $R^{1b}$, $R^{2a}$, $R^{2b}$, $R^{3a}$, $R^{3b}$, $X^1$, $X^2$, the ring $Y^1$, the ring $Y^2$, R, and n1 to n6 are the same as those in the formula (a1)) is preferable.

Furthermore, the aromatic amine compound represented by the formula (a4), a compound represented by the following formula (a6):

[Chem. 10]

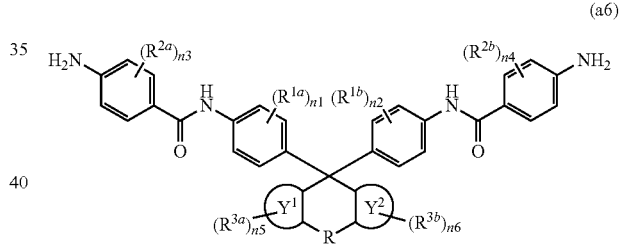

(a6)

(wherein, in the formula (a6), $R^{1a}$, $R^{1b}$, $R^{2a}$, $R^{2b}$, $R^{3a}$, $R^{3b}$, $X^1$, $X^2$, a ring $Y^1$, a ring $Y^2$, R, and n1 to n6 are the same as those in the formula (a1)) is preferable.

Specific preferable examples of the aromatic amine compound represented by the formula (a1) described above include a fluorene compound having the two same substituents at the position 9 of the following formula.

[Chem. 11]

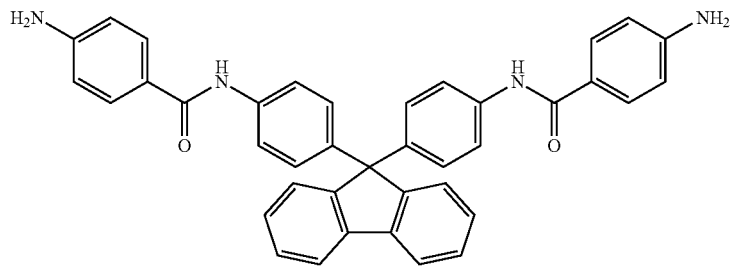

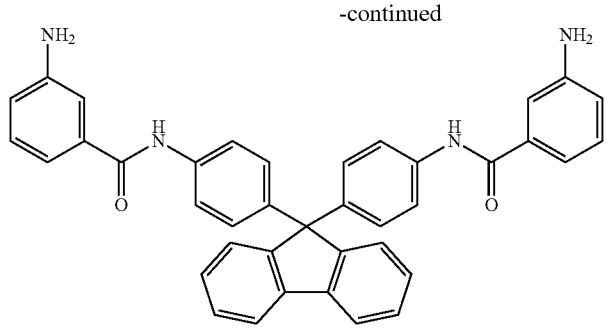
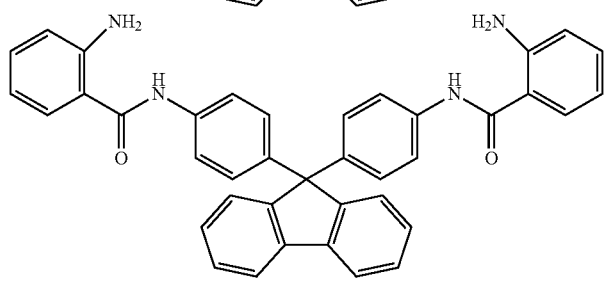
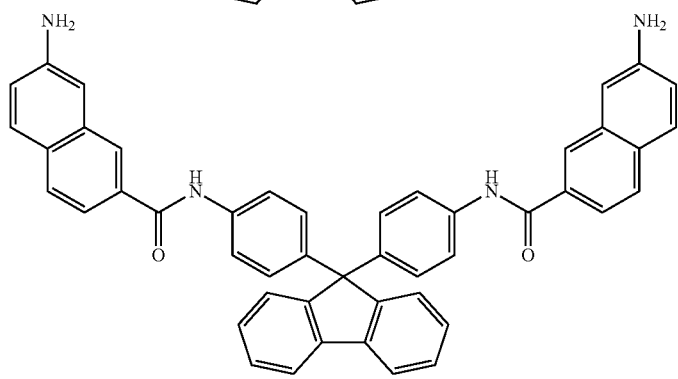
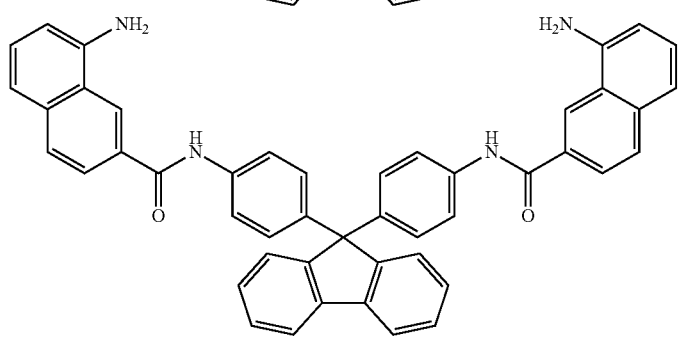
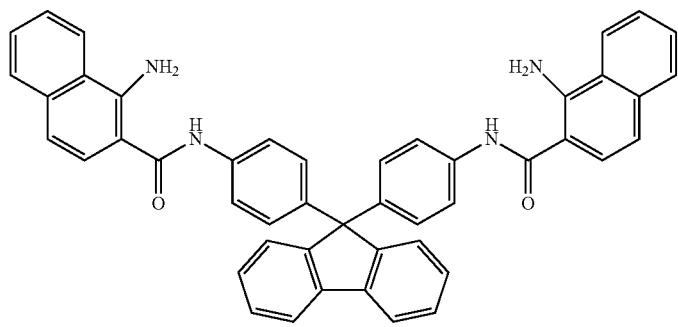

-continued
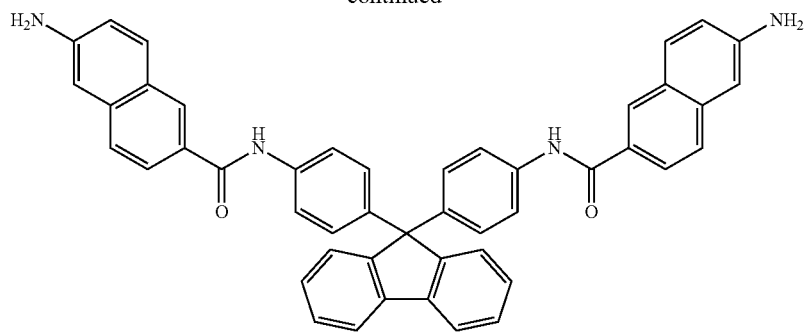
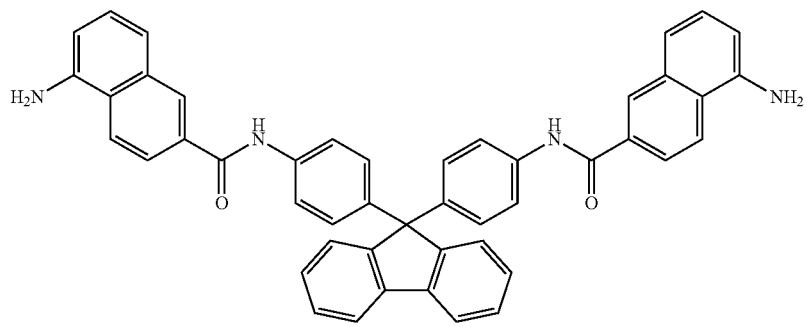
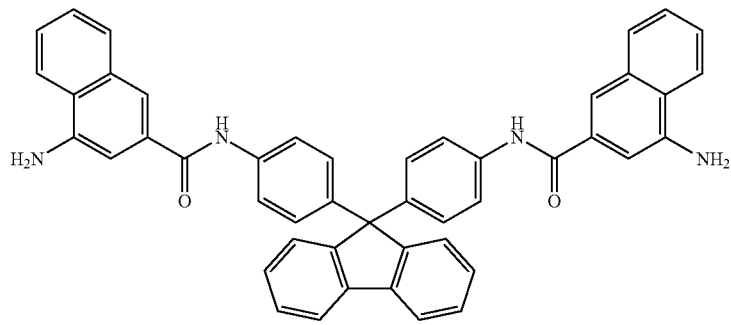
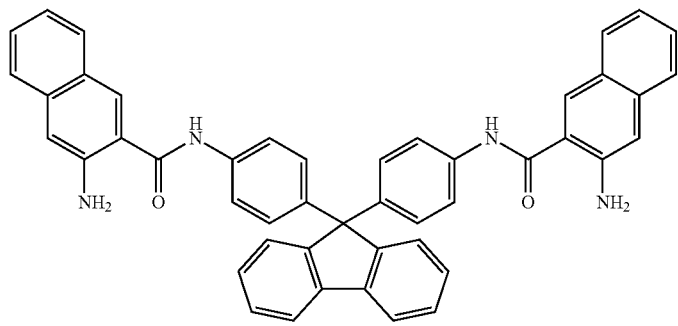
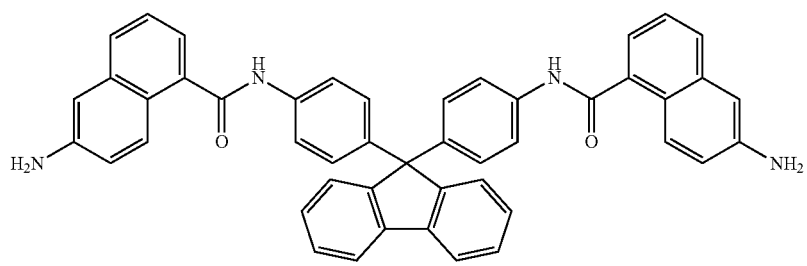

-continued
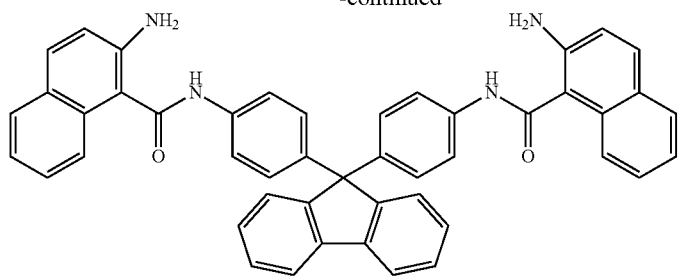
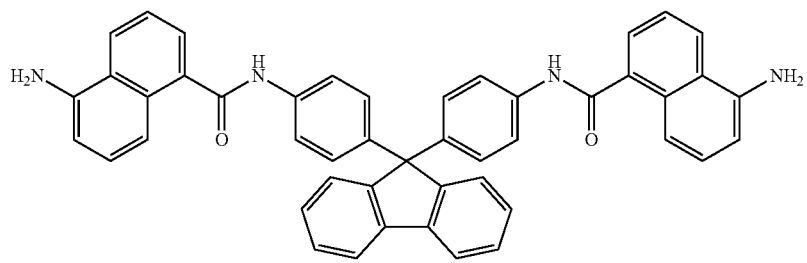
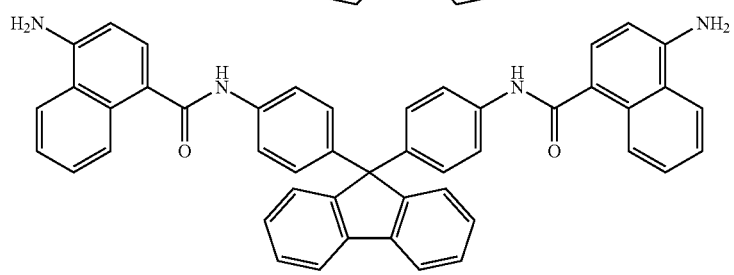
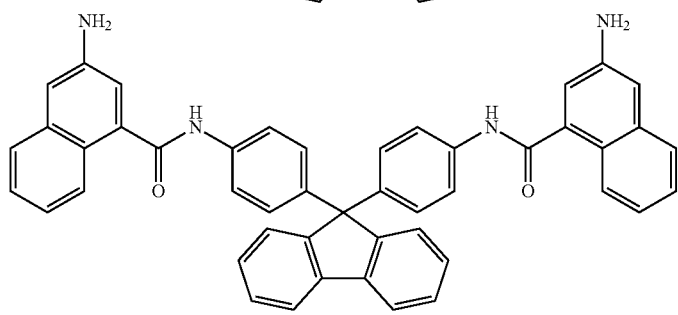
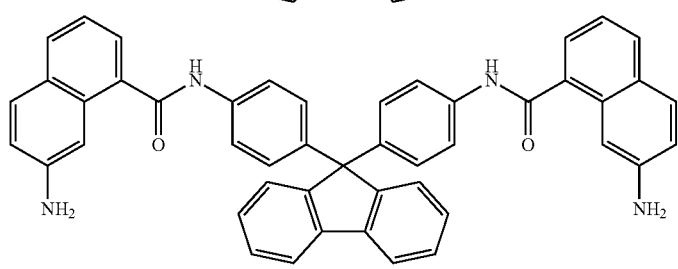
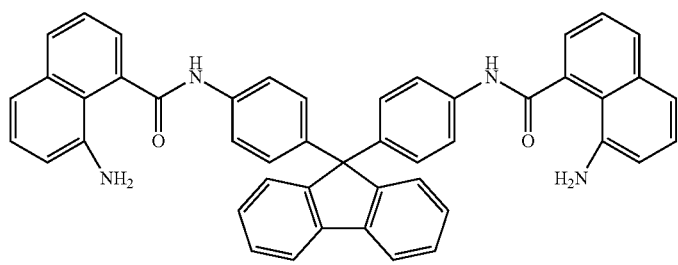

-continued
[Chem. 12]
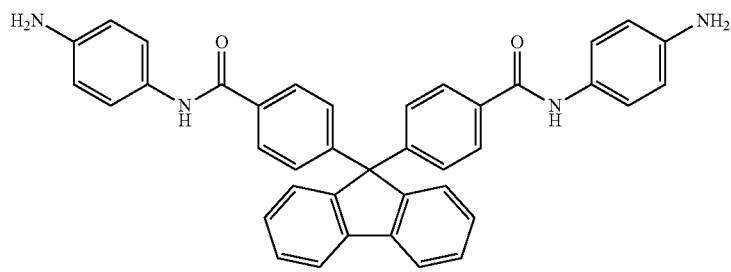
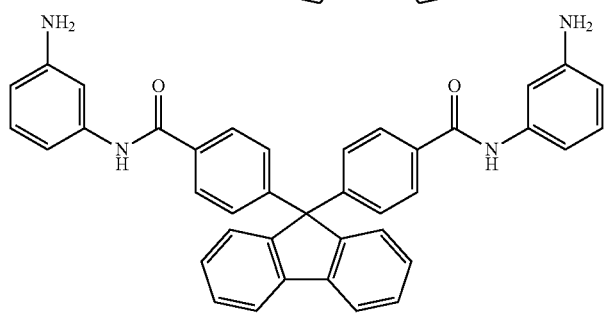
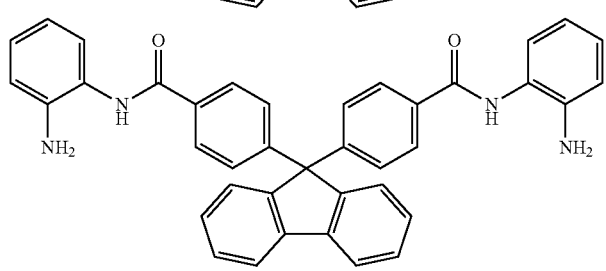
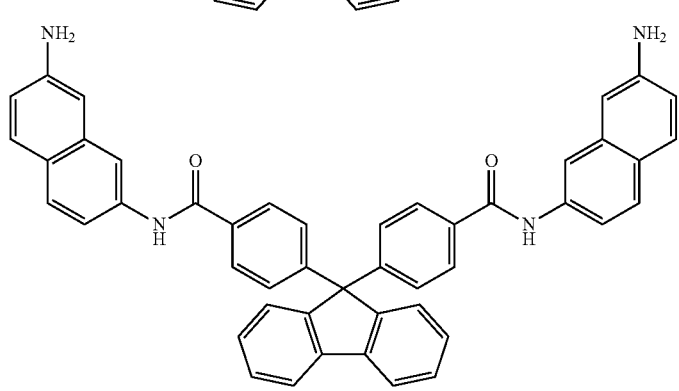
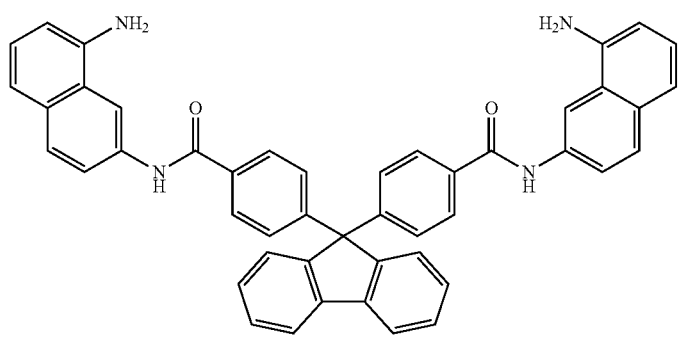

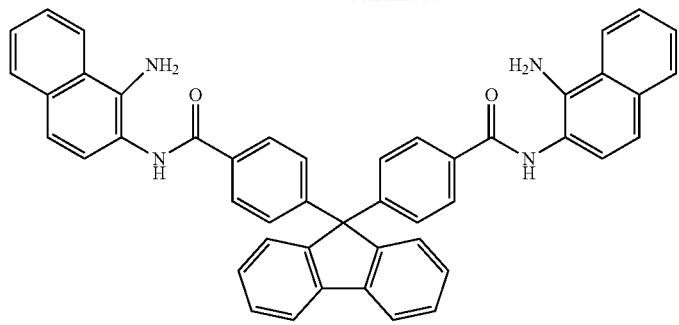
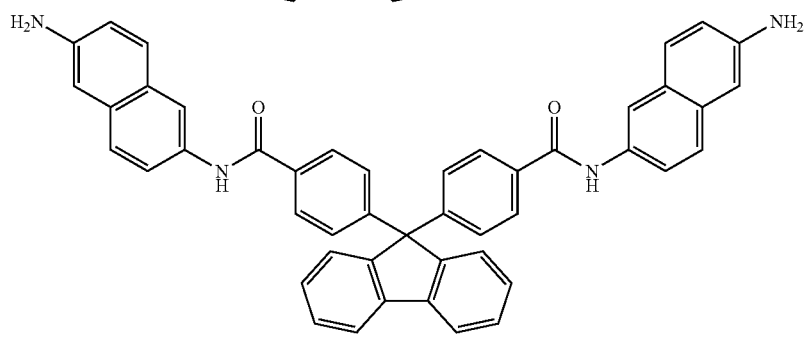
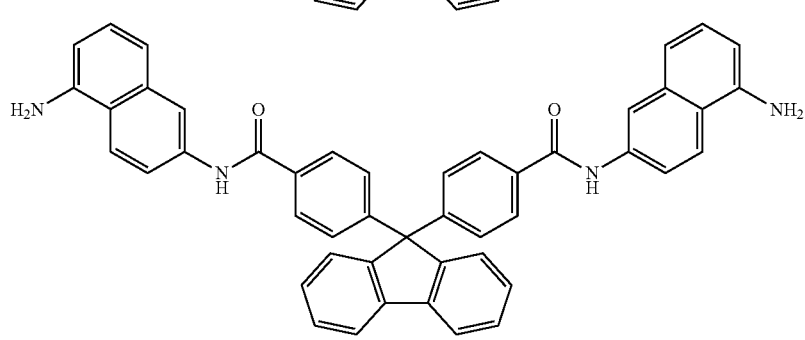
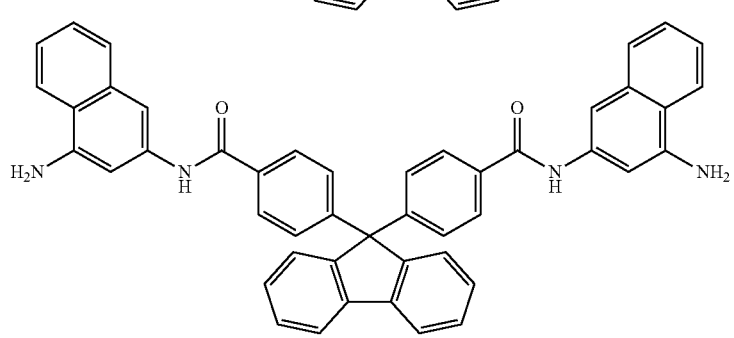
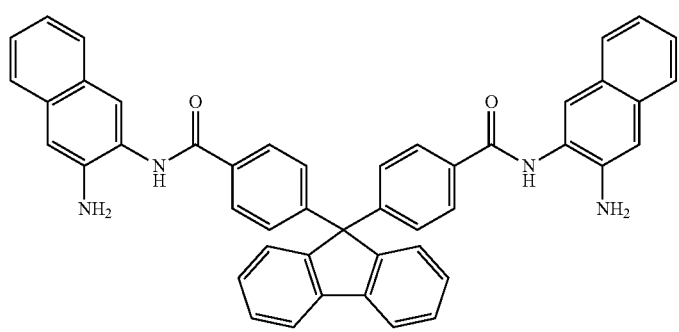

-continued
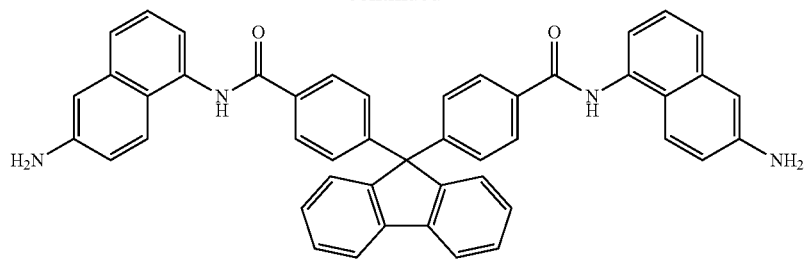
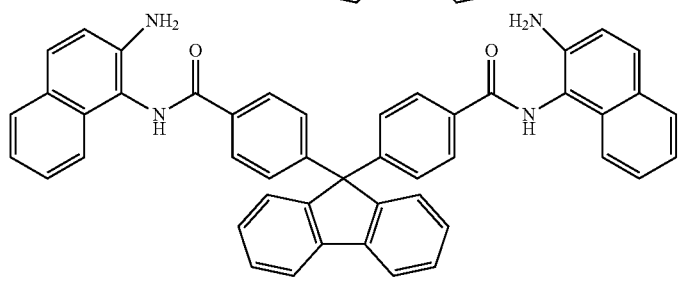
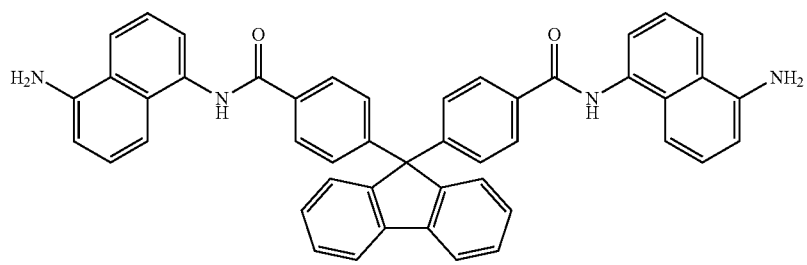
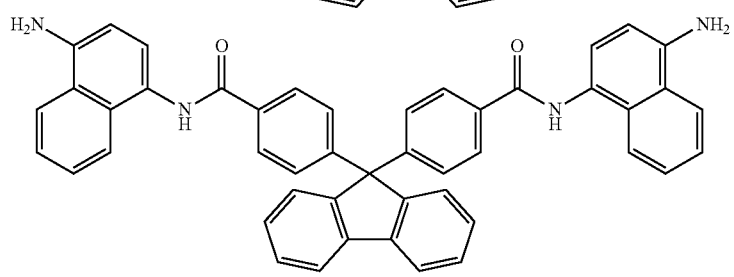
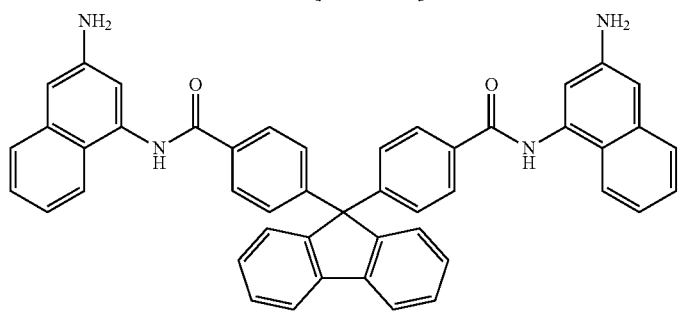
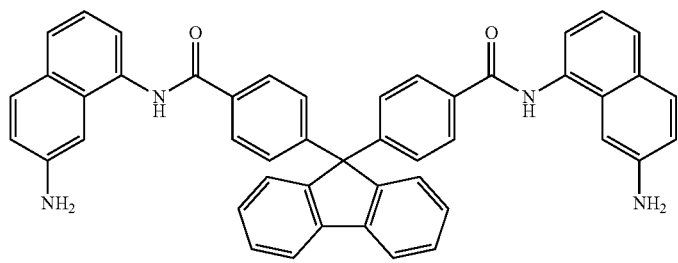

-continued

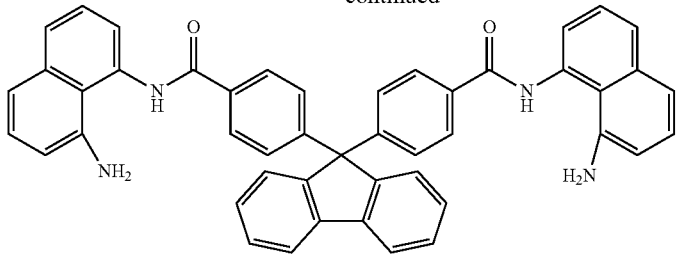

Compounds in which an amide bond (—CO—NH—) is substituted by —CO—O—, —NH—CO—NH—, —CO—NH—CO—, —O—CO—NH—, or —CO—NH—CO—NH— in the above-mentioned compounds are also suitable examples of the compound represented by the formula (a1).

<<Curing Agent for Epoxy Compound>>

A curing agent for an epoxy compound is not particularly limited as long as it includes a compound represented by the formula (a1) described above. Only the compound represented by the formula (a1) may be used as the curing agent for an epoxy compound. Furthermore, the curing agent for an epoxy compound may include various components other than the compound represented by the formula (a1), for example, a compound capable of curing an epoxy compound and an organic solvent. For example, the curing agent for an epoxy compound may include an antioxidant, an ultraviolet absorber, a viscosity modifier, an anti-foaming agent, a surfactant, and the like, in a range in which they do not inhibit performance as the curing agent for an epoxy compound. Examples of the organic solvent include organic solvents that are the same as those which the below-mentioned curable composition may include.

The curing agent for an epoxy compound may include a curing accelerator. Examples of the curing accelerator include a urea compound, tertiary amine and a salt thereof, imidazoles and salt thereof, phosphine compounds and derivatives thereof, carboxylic acid metal salt, Lewis acid, Bronsted acids and the salts thereof, tetraphenyl boron salt, and the like.

The content of the compound represented by the formula (a1) in the curing agent for an epoxy compound is preferably 70% by mass or more, more preferably 80% by mass or more, particularly preferably 90% by mass or more, and the most preferably 95% by mass or more with respect to the mass of the curing agent for an epoxy compound excluding the organic solvent.

<<Curable Compositions>>

A curable composition includes an (A) epoxy compound and a (B) curing agent. The (B) curing agent is the curing agent for an epoxy compound described above.

<(A) Epoxy Compound>

An (A) epoxy compound is not particularly limited as long as the compound has an epoxy group. The (A) epoxy compound can be selected from various compounds having an epoxy group which has been blended in a curable composition conventionally. The (A) epoxy compound may be a low molecular weight compound having an epoxy group which is a non-polymer or may be a polymer having an epoxy group. Hereinafter, in regard to the (A) epoxy compound, a non-polymer having an epoxy group and a polymer having an epoxy group will be sequentially described.

[Non-Polymer Having Epoxy Group]

As a non-polymer having an epoxy group, an aliphatic epoxy compound not containing an aromatic group is preferable from a viewpoint of excellent mechanical characteristics of a cured product formed using a curable composition. Among the aliphatic epoxy compounds, an aliphatic epoxy compound having an alicyclic epoxy group is preferable from a viewpoint of forming a cured product with excellent transparency and hardness.

Specific examples of the aliphatic epoxy compound having an alicyclic epoxy group include 2-(3,4-epoxycyclohexyl-5,5-spiro-3,4-epoxy)cyclohexane-meth-dioxane, bis(3,4-epoxycyclohexylmethyl)adipate, bis(3,4-epoxy-6-methylcyclohexylmethyl)adipate, 3,4-epoxy-6-methylcyclohexyl-3',4'-epoxy-6'-methylcyclohexane carboxylate, s-caprolactone-modified 3,4-epoxycyclohexylmethyl-3',4'-epoxycyclohexane carboxylate, trimethylcaprolactone-modified 3,4-epoxycyclohexylmethyl-3',4'-epoxycyclohexane carboxylate, β-methyl-5-valerolactone-modified 3,4-epoxycyclohexylmethyl-3',4'-epoxycyclohexane carboxylate, methylenebis(3,4-epoxycyclohexane), di(3,4-epoxycyclohexylmethyl)ether of ethylene glycol, ethylenebis(3,4-epoxycyclohexane carboxylate), dioctyl epoxycyclohexahydrophthalate, di-2-ethylhexyl epoxycyclohexahydrophthalate, an epoxy resin having a tricyclodecene oxide group, and a compound represented by the following formulae (A-1-1) to (A1-5). These alicyclic epoxy compounds may be used alone or in combination of two or more kinds thereof.

[Chem. 13]

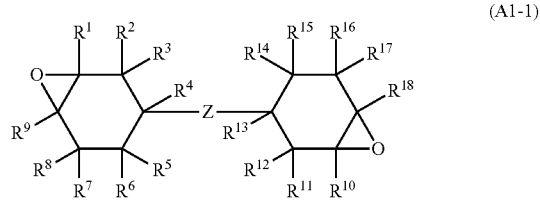

(A1-1)

In the formula (A1-1), Z is a single bond or a linking group (divalent group having one or more atoms). $R^1$ to $R^{18}$ are each independently a group selected from the group consisting of a hydrogen atom, a halogen atom and an organic group.

Examples of linking group Z include a divalent group selected from the group consisting of a divalent hydrocarbon group, —O—, —O—CO—, —S—, —SO—, —SO$_2$—, —CBr$_2$—, —C(CBr$_3$)$_2$—, —C(CF$_3$)$_2$, and —R$^{19}$—O—CO—, a group formed by bonding plurality of these divalent groups, and the like.

Examples of the divalent hydrocarbon group as the linking group Z can include a linear or branched alkylene group having 1 or more and 18 or less carbon atoms, a divalent alicyclic hydrocarbon group and the like. Examples of the linear or branched alkylene group having 1 or more and 18 or less carbon atoms include a methylene group, a methylmethylene group, a dimethylmethylene group, a dimethylene group, a trimethylene group, and the like. Examples of the above-described divalent alicyclic hydrocarbon group include a cycloalkylene group (including a cydlohexylidene group) such as a 1,2-cyclopentylene group, a 1,3-cyclopentylene group, a cyclopentylidene group, a 1,2-cyclohexylene group, 1,3-cyclohexylene group, 1,4-cyclohexylene group, and a cyclohexylidene group.

$R^{19}$ is an alkylene group having 1 or more and 8 or less carbon atoms and preferably a methylene group or an ethylene group.

[Chem. 14]

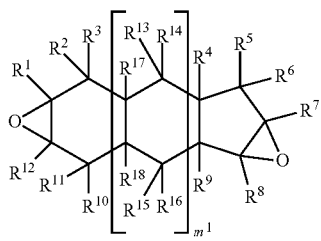

(A1-2)

(In the formula (A1-2), $R^1$ to $R^{18}$ are a group selected from the group consisting of a hydrogen atom, a halogen atom, and an organic group. $R^2$ and $R^{10}$ may be bonded to each other to form a ring. $R^{13}$ and $R^{16}$ may be bonded to each other to form a ring, $m^1$ is 0 or 1.)

[Chem. 15]

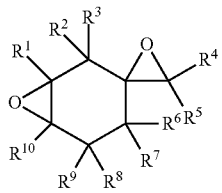

(A1-3)

(In the formula (A1-3), $R^1$ to $R^{10}$ are a group selected from the group consisting of a hydrogen atom, a halogen atom, and an organic group. $R^2$ and $R^8$ may be bonded to each other to form a ring.)

[Chem. 16]

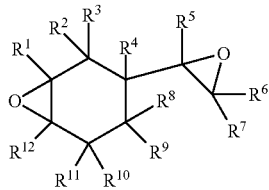

(A1-4)

(In the formula (A1-4), $R^1$ to $R^{12}$ are a group selected from the group consisting of a hydrogen atom, a halogen atom, and an organic group. $R^2$ and $R^{10}$ may be bonded to each other to form a ring.)

[Chem. 17]

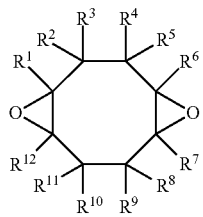

(A1-5)

(In the formula (A1-5), $R^1$ to $R^{12}$ are a group selected from the group consisting of a hydrogen atom, a halogen atom, and an organic group.)

In the formulae (A1-1) to (A1-5), when $R^1$ to $R^{18}$ are organic groups, the organic group is not particularly limited as long as the object of the present invention is not impaired, and may be a hydrocarbon group, or a group consisting of a carbon atom and a halogen atom, or a group having heteroatoms such as a halogen atom, an oxygen atom, a sulfur atom, a nitrogen atom, and a silicon atom, together with a carbon atom and a hydrogen atom. Examples of the halogen atom include a chlorine atom, a bromine atom, an iodine atom, and a fluorine atom.

The organic group is preferably a group consisting of a hydrocarbon group, a group consisting of a carbon atom, a hydrogen atom, and an oxygen atom, a halogenated hydrocarbon group, a group consisting of a carbon atom, an oxygen atom, and a halogen atom, and a group consisting of a carbon atom, a hydrogen atom, an oxygen atom, and a halogen atom. When the organic group is a hydrocarbon group, the hydrocarbon group may be an aromatic hydrocarbon group, or an aliphatic hydrocarbon group, or a group including an aromatic skeleton and an aliphatic skeleton. The number of carbon atoms of the organic group is preferably 1 or more and 20 or less, more preferably 1 or more and 10 or less, and particularly preferably 1 or more and 5 or less.

Specific examples of the hydrocarbon group include chain alkyl groups such as a methyl group, an ethyl group, an n-propyl group, an isopropyl group, an n-butyl group, an isobutyl group, a sec-butyl group, a tert-butyl group, an n-pentyl group, an n-hexyl group, an n-heptyl group, an n-octyl group, a 2-ethylhexyl group, an n-nonyl group, an n-decyl group, an n-undecyl group, an n-tridecyl group, an n-tetradecyl group, an n-pentadecyl group, an n-hexadecyl group, an n-heptadecyl group, an n-octadecyl group, an n-nonadecyl group, and an n-icosyl group; chain alkenyl groups such as a vinyl group, a 1-propenyl group, a 2-n-propenyl group (allyl group), a 1-n-butenyl group, a 2-n-butenyl group, and a 3-n-butenyl group; cycloalkyl groups such as a cyclopropyl group, a cyclobutyl group, a cyclopentyl group, a cyclohexyl group, and a cycloheptyl group; aryl groups such as a phenyl group, an o-tolyl group, an m-tolyl group, a p-tolyl group, an α-naphthyl group, a β-naphthyl group, a biphenyl-4-yl group, a biphenyl-3-yl group, a biphenyl-2-yl group, an anthryl group, and a phenanthryl group; and aralkyl groups such as a benzyl group, a phenethyl group, an α-naphthylmethyl group, a β-naphthylmethyl group, an α-naphthylethyl group, and a β-naphthylethyl group.

Specific examples of the halogenated hydrocarbon group include halogenated chain alkyl groups such as a chloromethyl group, a dichloromethyl group, a trichloromethyl group, a bromomethyl group, a dibromomethyl group, a tribromomethyl group, a fluoromethyl group, a difluoromethyl group, a trifluoromethyl group, a 2,2,2-trifluoroethyl group, a pentafluoroethyl group, a heptafluoropropyl group, a perfluorobutyl group, and a perfluoropentyl group, a perfluorohexyl group, a perfluoroheptyl group, a perfluorooctyl group, a perfluorononyl group, and a perfluorodecyl group; halogenated cycloalkyl groups such as a 2-chlorocyclohexyl group, a 3-chlorocyclohexyl group, a 4-chlorocyclohexyl group, a 2,4-dichlorocyclohexyl group, a 2-bromocyclohexyl group, a 3-bromocyclohexyl group, and a 4-bromocyclohexyl group; halogenated aryl groups such as a 2-chlorophenyl group, a 3-chlorophenyl group, a 4-chlorophenyl group, a 2,3-dichlorophenyl group, a 2,4-dichlorophenyl group, a 2,5-dichlorophenyl group, a 2,6-dichlorophenyl group, a 3,4-dichlorophenyl group, a 3,5-dichlorophenyl group, a 2-bromophenyl group, a 3-bromophenyl group, a 4-bromophenyl group, a 2-fluorophenyl group, a 3-fluorophenyl group, and a 4-fluorophenyl group; and halogenated aralkyl groups such as a 2-chlorophenylmethyl group, a 3-chlorophenylmethyl group, a 4-chlorophenylmethyl group, a 2-bromophenylmethyl group, a 3-bromophenylmethyl group, a 4-bromophenylmethyl group, a 2-fluorophenylmethyl group, a 3-fluorophenylmethyl group, and a 4-fluorophenylmethyl group.

Specific examples of the group consisting of a carbon atom, a hydrogen atom, and an oxygen atom include hydroxy chain alkyl groups such as a hydroxymethyl group, a 2-hydroxyethyl group, a 3-hydroxy-n-propyl group, and a 4-hydroxy-n-butyl group; halogenated cycloalkyl groups such as a 2-hydroxycyclohexyl group, a 3-hydroxycyclohexyl group, and a 4-hydroxycyclohexyl group; hydroxyaryl groups such as a 2-hydroxyphenyl group, a 3-hydroxyphenyl group, a 4-hydroxyphenyl group, a 2,3-dihydroxyphenyl group, a 2,4-dihydroxyphenyl group, a 2,5-dihydroxyphenyl group, a 2,6-dihydroxyphenyl group, a 3,4-dihydroxyphenyl group, and a 3,5-dihydroxyphenyl group; hydroxyaralkyl groups such as a 2-hydroxyphenylmethyl group, a 3-hydroxyphenylmethyl group, and a 4-hydroxyphenylmethyl group; chain alkoxy groups such as a methoxy group, an ethoxy group, an n-propoxy group, an isopropoxy group, an n-butyloxy group, an isobutyloxy group, a sec-butyloxy group, a tert-butyloxy group, an n-pentyloxy group, an n-hexyloxy group, an n-heptyloxy group, an n-octyloxy group, a 2-ethylhexyloxy group, an n-nonyloxy group, an n-decyloxy group, an n-undecyloxy group, an n-tridecyloxy group, an n-tetradecyloxy group, an n-pentadecyloxy group, an n-hexadecyloxy group, an n-heptadecyloxy group, an n-octadecyloxy group, an n-nonadecyloxy group, and an n-icosyloxy group; chain alkenyloxy groups such as a vinyloxy group, a 1-propenyloxy group, a 2-n-propenyloxy group (allyloxy group), a 1-n-butenyloxy group, a 2-n-butenyloxy group, and a 3-n-butenyloxy group; aryloxy groups such as a phenoxy group, an o-tolyloxy group, an m-tolyloxy group, a p-tolyloxy group, an α-naphthyloxy group, a β-naphthyloxy group, a biphenyl-4-yloxy group, a biphenyl-3-yloxy group, a biphenyl-2-yloxy group, an anthryloxy group, and a phenanthryloxy group; aralkyloxy groups such as a benzyloxy group, a phenethyloxy group, an α-naphthylmethyloxy group, a β-naphthylmethyloxy group, an α-naphthylethyloxy group, and a β-naphthylethyloxy group; alkoxyalkyl groups such as a methoxymethyl group, an ethoxymethyl group, an n-propoxymethyl group, a 2-methoxyethyl group, a 2-ethoxyethyl group, a 2-n-propoxyethyl group, a 3-methoxy-n-propyl group, a 3-ethoxy-n-propyl group, a 3-n-propoxy-n-propyl group, a 4-methoxy-n-butyl group, a 4-ethoxy-n-butyl group, and a 4-n-propoxy-n-butyl group; alkoxyalkoxy groups such as a methoxymethoxy group, an ethoxymethoxy group, an n-propoxymethoxy group, a 2-methoxyethoxy group, a 2-ethoxyethoxy group, a 2-n-propoxyethoxy group, a 3-methoxy-n-propoxy group, a 3-ethoxy-n-propoxy group, a 3-n-propoxy-n-propoxy group, a 4-methoxy-n-butyloxy group, a 4-ethoxy-n-butyloxy group, and a 4-n-propoxy-n-butyloxy group; alkoxyaryl groups such as a 2-methoxyphenyl group, a 3-methoxyphenyl group, and a 4-methoxyphenyl group; alkoxyaryloxy groups such as a 2-methoxyphenoxy group, a 3-methoxyphenoxy group, and a 4-methoxyphenoxy group; aliphatic acyl groups such as a formyl group, an acetyl group, a propionyl group, a butanoyl group, a pentanoyl group, a hexanoyl group, a heptanoyl group, an octanoyl group, a nonanoyl group, and a decanoyl group; aromatic acyl groups such as a benzoyl group, an α-naphthoyl group, and a β-naphthoyl group; chain alkyloxycarbonyl groups such as a methoxycarbonyl group, an ethoxycarbonyl group, an n-propoxycarbonyl group, an n-butyloxycarbonyl group, an n-pentyloxycarbonyl group, an n-hexylcarbonyl group, an n-heptyloxycarbonyl group, an n-octyloxycarbonyl group, an n-nonyloxycarbonyl group, and an n-decyloxycarbonyl group; aryloxycarbonyl groups such as a phenoxycarbonyl group, an α-naphthoxycarbonyl group, and a β-naphthoxycarbonyl group; aliphatic acyloxy groups such as a formyloxy group, an acetyloxy group, a propionyloxy group, a butanoyloxy group, a pentanoyloxy group, a hexanoyloxy group, a heptanoyloxy group, an octanoyloxy group, a nonanoyloxy group, and a decanoyloxy group; and aromatic acyloxy groups such as a benzoyloxy group, an α-naphthoyloxy group, and a β-naphthoyloxy group.

It is preferable that $R^1$ to $R^{18}$ each independently represent a group selected from the group consisting of a hydrogen atom, a halogen atom, an alkyl group having 1 or more and 5 or less carbon atoms, and an alkoxy group having 1 or more and 5 or less carbon atoms. It is more preferable that $R^1$ to $R^{18}$ all are a hydrogen atom because a cured film that is particularly excellent in mechanical characteristics can be easily formed.

In the formulae (A1-2) to (A1-5), $R^1$ to $R^{18}$ are the same as $R^1$ to $R^{18}$ in the formula (A1-1). When $R^2$ and $R^{10}$ are bonded to each other in the formulae (A1-2) and (A1-4), when $R^{13}$ and $R^{16}$ are bonded to each other in the formula (A1-2), and when $R^2$ and $R^8$ are bonded to each other in the formula (A1-3), examples of the divalent group formed by bonding of two groups include —CH$_2$— and —C(CH$_3$)$_2$—.

Specific examples of a suitable compound for the alicyclic epoxy compounds represented by the formula (A1-1) include alicyclic epoxy compounds represented by the following formulae (A1-1a), (A1-1b) and (A1-1c), 2,2-bis(3,4-epoxycyclohexane-1-yl)propane [=2,2-bis(3,4-epoxy-epoxycyclohexyl) propane], and the like.

[Chem. 18]

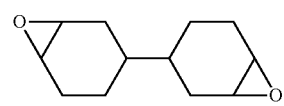

(A1-1a)

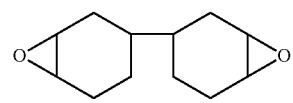

(A1-1b)

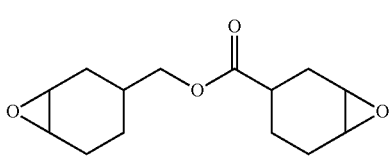

(A1-1c)

Specific examples of a suitable compound in the alicyclic epoxy compounds represented by the formula (A1-2) include compounds represented by the following formula (A1-2a) or the following formula (A1-2b).

[Chem. 19]

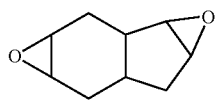

(A1-2a)

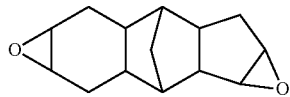

(A1-2b)

Specific examples of suitable compound for the alicyclic epoxy compounds represented by the formula (A1-3) include S-spiro[3-oxatricyclo[3.2.1.0$^{2,4}$]octane-6,2'-oxirane], and the like.

Specific examples of suitable compound for the alicyclic epoxy compounds represented by the formula (A1-4) include 4-vinylcyclohexene dioxide, dipentene dioxide, limonene dioxide, 1-methyl-4-(3-methyloxirane-2-yl)-7-oxabicyclo[4.1.0]heptane, and the like.

Specific examples of suitable compound for the alicyclic epoxy compounds represented by the formula (A1-5) include 1,2,5,6-diepoxycyclooctane, and the like.

Examples of the non-polymer which can be suitably used as the (A) epoxy compound and has an epoxy group other than the aliphatic epoxy compounds having the above-described alicyclic epoxy groups, include epoxy alkyl (meth)acrylate such as glycidyl (meth)acrylate, 2-methylglycidyl(meth)acrylate, 3,4-epoxybutyl (meth)acrylate, or 6,7-epoxyheptyl(meth)acrylate; epoxy alkyloxy alkyl (meth)acrylate such as 2-glycidyloxyethyl(meth)acrylate, 3-glycidyloxy-n-propyl(meth)acrylate, 4-glycidyloxy-n-butyl(meth)acrylate, 5-glycidyloxy-n-hexyl(meth)acrylate, or 6-glycidyloxy-n-hexyl(meth)acrylate; a bifunctional epoxy resin such as a bisphenol A type epoxy resin, a bisphenol F type epoxy resin, a bisphenol S type epoxy resin, a bisphenol AD type epoxy resin, a naphthalene type epoxy resin, or a biphenyl type epoxy resin; a novolac epoxy resin such as a phenol novolac type epoxy resin, a brominated phenol novolac type epoxy resin, a ortho-cresol novolac type epoxy resin, a bisphenol A novolac type epoxy resin, or a bisphenol AD novolac type epoxy resin; a cyclic aliphatic epoxy resin such as an epoxide of a dicyclopentadiene type phenol resin; an aromatic epoxy resin such as an epoxide of a naphthalene type phenol resin; an epoxy group-containing fluorene compound such as 9,9-bis[4-(glycidyloxy)phenyl]-9H-fluorene, 9,9-bis[4-[2-(glycidyloxy)ethoxy]phenyl]-9H-fluorene, 9,9-bis[4-[2-(glycidyloxy)ethyl]phenyl]-9H-fluorene, 9,9-bis[4-(glycidyloxy)-3-methylphenyl]-9H-fluorene, 9,9-bis[4-(glycidyloxy)-3,5-dimethylphenyl]-9H-fluorene, and 9,9-bis(6-glycidyloxy naphthalene-2-yl)-9H-fluorene; a glycidyl ester type epoxy resin such as dimer acid glycidyl ester or triglycidyl ester; a glycidyl amine type epoxy resin such as tetraglycidylamino diphenyl methane, triglycidyl-p-aminophenol, tetraglycidyl metaxylylene diamine, or tetraglycidyl bisaminomethyl cyclohexane; a heterocyclic epoxy resin such as triglycidyl isocyanurate; a trifunctional epoxy resin such as phloroglucinol triglycidyl ether, trihydroxy biphenyl triglycidyl ether, trihydroxy phenyl methane triglycidyl ether, glycerin triglycidyl ether, 2-[4-(2,3-epoxypropoxy)phenyl]-2-[4-[1,1-bis[4-(2,3-epoxypropoxy)phenyl]ethyl]phenyl]propane, or 1,3-bis[4-[1-[4-(2,3-epoxypropoxy)phenyl]-1-[4-[1-[4-(2,3-epoxypropoxy)phenyl]-1-methylethyl]phenyl]ethyl]phenoxy]-2-propanol; a tetrafunctional epoxy resin such as tetrahydroxy phenyl ethane tetraglycidyl ether, tetraglycidyl benzophenone, bisresorcinol tetraglycidyl ether, or tetraglycidoxy biphenyl; and 1,2-epoxy-4-(2-oxiranyl)cyclohexane adduct of 2,2-bis(hydroxymethyl)-1-butanol. 1,2-Epoxy-4-(2-oxiranyl)cyclohexane adduct of 2,2-bis(hydroxymethyl)-1-butanol is commercially available as EHPE-3150 (manufactured by Daicel Corporation).

[Polymer Having Epoxy Group]

A polymer having an epoxy group may be a polymer obtained by polymerizing a monomer having an epoxy group or a monomer mixture that contains a monomer having an epoxy group or may be a polymer in which an epoxy group is introduced using a compound having an epoxy group such as epichlorohydrin with respect to a polymer having a functional group with reactivity such as a hydroxyl group, a carboxy group, or an amino group. Furthermore, a partial oxide of a polymer having an unsaturated aliphatic hydrocarbon group in the side chain such as 1,2-polybutadiene can be suitably used as a polymer having an epoxy group. Such a partial oxide contains an epoxy group formed due to oxidation of an unsaturated bond contained in the side chain.

As a polymer having an epoxy group, a polymer obtained by polymerizing a monomer having an epoxy group or a monomer mixture containing a monomer having an epoxy group or a partial oxide of a polymer having an unsaturated aliphatic hydrocarbon group in the side chain is preferable from a viewpoint of ease of obtainment, preparation, or adjustment of the amount of an epoxy group in a polymer.

The partial oxide of the polymer having an unsaturated aliphatic hydrocarbon group in the side chain is preferably partial oxide of 1,2-polybutadiene having a vinyl group in the side chain from the viewpoint of easy availability and easy synthesis, and the like. Epoxidized polybutadiene having an oxiranyl group and a vinyl group in the side chain can be obtained by partially oxidizing 1,2-polybutadiene. The ratio of the oxiranyl group in such an epoxidized polybutadiene is preferably 10% by mole or more and 70% by mole or less, more preferably 10% by mole or more and 50% by mole or less, and still more preferably 10% by mole or more and 40% by mole or less based on the total number of moles of the oxiranyl group and the vinyl group. As the epoxidized polybutadiene, commercially available JP-100 or JP-200 (manufactured by NIPPON SODA CO., LTD.) can be suitably used.

Among the polymers having an epoxy group, because of easiness in preparation, a homopolymer of a (meth)acrylic acid ester having an epoxy group, or a copolymer of a (meth)acrylic acid ester having an epoxy group and other monomers are preferable.

The (meth)acrylic acid ester having an epoxy group may be either a chain aliphatic (meth)acrylic acid ester having an epoxy group, or the below-mentioned (meth)acrylic acid ester having an alicyclic epoxy group. The (meth)acrylic acid ester having an epoxy group may have an aromatic group. The (meth)acrylic acid ester having an epoxy group is preferably an aliphatic (meth)acrylic acid ester having a chain aliphatic epoxy group or an aliphatic (meth)acrylic acid ester having an alicyclic epoxy group, and more preferably an aliphatic (meth)acrylic acid ester having an alicyclic epoxy group.

Examples of the (meth)acrylic acid ester, which has an aromatic group and an epoxy group, include 4-glycidyloxyphenyl (meth)acrylate, 3-glycidyloxyphenyl (meth)acrylate, 2-glycidyloxyphenyl (meth)acrylate, 4-glycidyloxyphenylmethyl (meth)acrylate, 3-glycidyloxyphenylmethyl (meth)acrylate, and 2-glycidyloxyphenylmethyl (meth)acrylate.

Examples of the aliphatic (meth)acrylic acid ester having a chain aliphatic epoxy group include (meth)acrylic acid esters in which a chain aliphatic epoxy group is combined with an oxy group (—O—) in an ester group (—O—CO—), such as epoxyalkyl (meth)acrylate and epoxyalkyloxyalkyl (meth)acrylate. Such a chain aliphatic epoxy group possessed by the (meth)acrylic acid ester may have one or plural oxy group(s) (—O—) in a chain. The number of carbon atoms of the chain aliphatic epoxy group is not particularly limited, and is preferably 3 or more and 20 or less, more preferably 3 or more and 15 or less, and particularly preferably 3 or more and 10 or less.

Specific examples of the aliphatic (meth)acrylic acid ester having a chain aliphatic epoxy group include epoxyalkyl (meth)acrylates such as glycidyl (meth)acrylate, 2-methyl glycidyl (meth)acrylate, 3,4-epoxybutyl (meth)acrylate, and 6,7-epoxyheptyl (meth)acrylate; and epoxyalkyloxyalkyl (meth)acrylates such as 2-glycidyloxyethyl (meth)acrylate, 3-glycidyloxy-n-propyl (meth)acrylate, 4-glycidyloxy-n-butyl (meth)acrylate, 5-glycidyloxy-n-hexyl (meth)acrylate, and 6-glycidyloxy-n-hexyl (meth)acrylate.

Specific examples of the aliphatic (meth)acrylic acid ester having an alicyclic epoxy group include compounds represented by the following formulae (A2-1) to (A2-15). Of these compounds, compounds represented by the following formulae (A2-1) to (A2-5) are preferable, and compounds represented by the following formulae (A2-1) to (A2-3) are more preferable.

[Chem. 20]

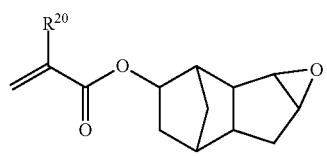
(A2-1)

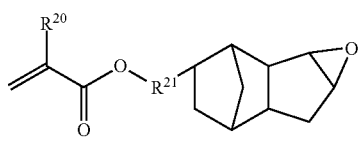
(A2-2)

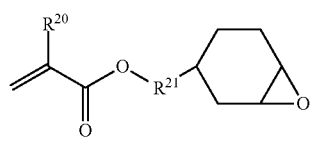
(A2-3)

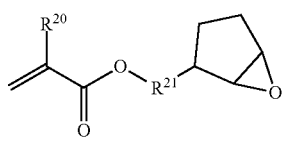
(A2-4)

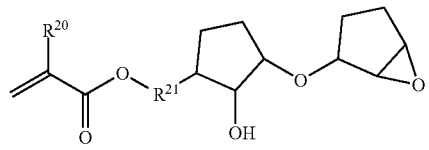
(A2-5)

[Chem. 21]

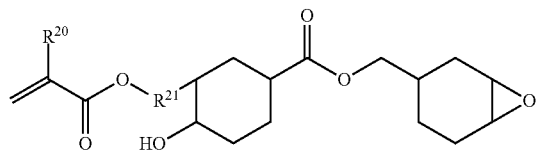
(A2-6)

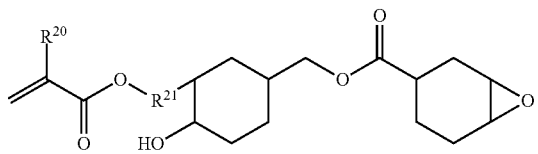
(A2-7)

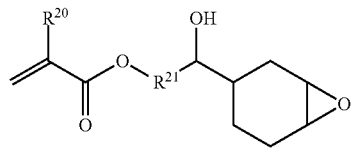
(A2-8)

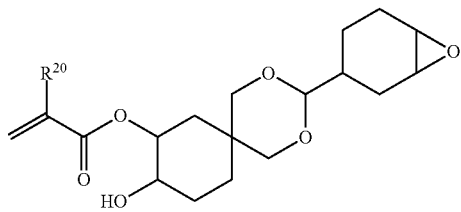
(A2-9)

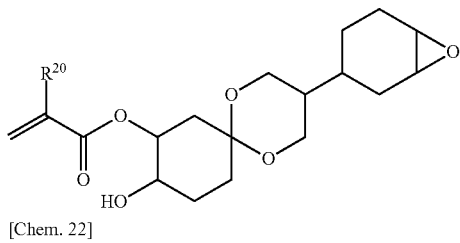
(A2-10)

[Chem. 22]

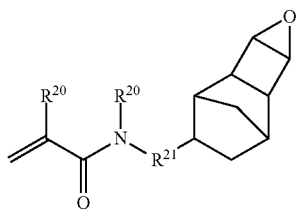
(A2-11)

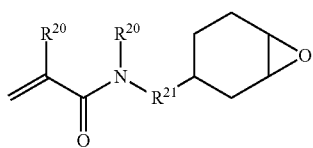
(A2-12)

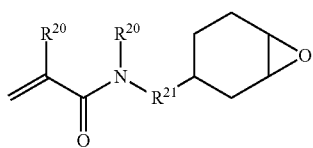
(A2-13)

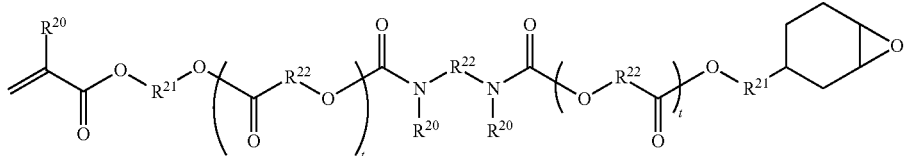
(A2-14)

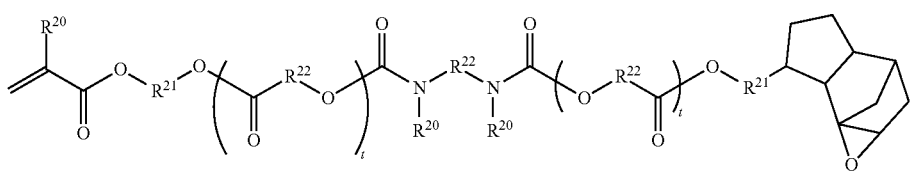
(A2-15)

In the above formulae, $R^{20}$ is a hydrogen atom or a methyl group; $R^{21}$ is a divalent aliphatic saturated hydrocarbon group having 1 or more and 6 or less carbon atoms; $R^{22}$ is a divalent hydrocarbon group having 1 or more and 10 or less carbon atoms; and t represents an integer of 0 or more and 10 or less. $R^{21}$ is a linear or branched alkylene group and is preferably, for example, a methylene group, an ethylene group, a propylene group, a tetramethylene group, an ethylethylene group, a pentamethylene group, or a hexamethylene group. $R^{22}$ is preferably, for example, a methylene group, an ethylene group, a propylene group, a tetramethylene group, an ethylethylene group, a pentamethylene group, a hexamethylene group, a phenylene group, or a cyclohexylene group.

It is possible to use, as the polymer having an epoxy group, both of a homopolymer of a (meth)acrylic acid ester having an epoxy group, and a copolymer of a (meth)acrylic acid ester having an epoxy group with the other monomer. The content of a unit derived from the (meth)acrylic acid ester having an epoxy group in the polymer having an epoxy group is preferably 70% by mass or more, more preferably 80% by mass or more, particularly preferably 90% by mass or more, and the most preferably 100% by mass.

When the polymer having an epoxy group is a copolymer of the (meth)acrylic acid ester having an epoxy group with the other monomer, examples of the other monomer include an unsaturated carboxylic acid, a (meth)acrylic acid ester having no epoxy group, (meth)acrylamides, an allyl compound, vinyl ethers, vinyl esters, styrenes, and the like. These compounds can be used alone, or two or more thereof can be used in combination. In view of storage stability of a curable composition, and chemical resistance of a cured film formed using the curable composition against alkali, it is preferable that the copolymer of the (meth)acrylic acid ester having an epoxy group with the other monomer does not include a unit derived from an unsaturated carboxylic acid.

Examples of the unsaturated carboxylic acid include (meth)acrylic acid; (meth)acrylic acid amide; crotonic acid; maleic acid, fumaric acid, citraconic acid, mesaconic acid, itaconic acid, and anhydrides of these dicarboxylic acids.

Examples of the (meth)acrylic acid ester having no epoxy group include linear or branched alkyl (meth)acrylates such as methyl (meth)acrylate, ethyl (meth)acrylate, propyl (meth)acrylate, amyl (meth)acrylate, and t-octyl (meth)acrylate; chloroethyl (meth)acrylate, 2,2-dimethylhydroxypropyl (meth)acrylate, 2-hydroxyethyl (meth)acrylate, trimethylolpropane mono(meth)acrylate, benzyl (meth)acrylate, furfuryl (meth)acrylate; and a (meth)acrylic acid ester having a group with an alicyclic skeleton. Of (meth)acrylic acid esters having no epoxy group, a (meth)acrylic acid ester having a group with an alicyclic skeleton is preferable.

In a (meth)acrylic acid ester having a group with an alicyclic skeleton, an alicyclic group composing the alicyclic skeleton may be either monocyclic or polycyclic. Examples of the monocyclic alicyclic group include a cyclopentyl group, a cyclohexyl group, and the like. Examples of the polycyclic alicyclic group include a norbornyl group, an isobornyl group, a tricyclononyl group, a tricyclodecyl group, a tetracyclododecyl group, and the like.

Examples of the (meth)acrylic acid ester having a group with an alicyclic skeleton include compounds represented by the following formulae (A3-1) to (A3-8). Among them, compounds represented by the following formulae (A3-3) to (A3-8) are preferable, and compounds represented by the following formulae (A3-3) or (A3-4) are more preferable.

[Chem. 23]

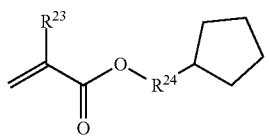
(A3-1)

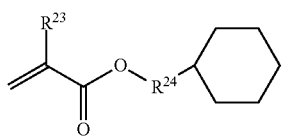
(A3-2)

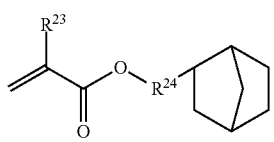
(A3-3)

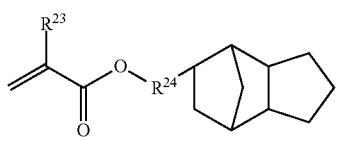
(A3-4)

[Chem. 24]

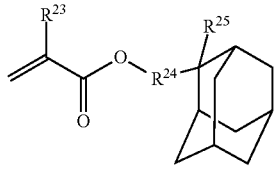
(A3-5)

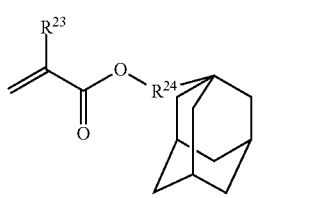
(A3-6)

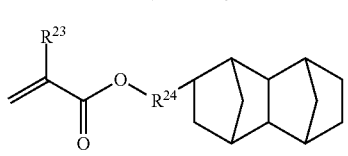
(A3-7)

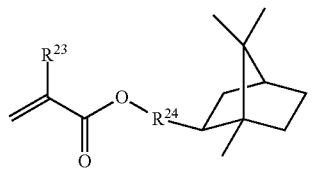
(A3-8)

In the above formulae, $R^{23}$ represents a hydrogen atom or a methyl group; $R^{24}$ represents a single bond or a divalent aliphatic saturated hydrocarbon group having 1 or more and 6 or less carbon atoms; and $R^{25}$ represents a hydrogen atom or an alkyl group having 1 or more and 5 or less carbon atoms. $R^{24}$ is preferably a single bond, or a linear or branched alkylene group, for example, a methylene group, an ethylene group, a propylene group, a tetramethylene group, an ethylethylene group, a pentamethylene group, or a hexamethylene group. $R^{25}$ is preferably a methyl group or an ethyl group.

Examples of (meth)acrylamides include (meth)acrylamide, N-alkyl(meth)acrylamide, N-aryl(meth)acrylamide, N,N-dialkyl(meth)acrylamide, N,N-aryl(meth)acrylamide, N-methyl-N-phenyl(meth)acrylamide, N-hydroxyethyl-N-methyl(meth)acrylamide, and the like.

Examples of the allyl compound include allyl esters such as allyl acetate, allyl caproate, allyl caprylate, allyl laurate, allyl palmitate, allyl stearate, allyl benzoate, allyl acetoacetate, and allyl lactate; allyloxyethanol, and the like.

Examples of vinyl ethers include aliphatic vinyl ethers such as hexyl vinyl ether, octyl vinyl ether, decyl vinyl ether, ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, hydroxyethyl vinyl ether, diethylene glycol vinyl ether, dimethylaminoethyl vinyl ether, diethylaminoethyl vinyl ether, butylaminoethyl vinyl ether, benzyl vinyl ether, and tetrahydrofurfuryl vinyl ether; vinylaryl ethers such as vinyl phenyl ether, vinyl tolyl ether, vinyl chlorophenyl ether, vinyl-2,4-dichlorophenyl ether, vinyl naphthyl ether, and vinyl anthranyl ether; and the like.

Examples of vinyl esters include vinyl butyrate, vinyl isobutyrate, vinyl trimethyl acetate, vinyl diethyl acetate, vinyl valerate, vinyl caproate, vinyl chloroacetate, vinyl dichloroacetate, vinyl methoxyacetate, vinyl butoxyacetate, vinyl phenylacetate, vinyl acetoacetate, vinyl lactate, vinyl-β-phenyl butyrate, vinyl benzoate, vinyl salicylate, vinyl chlorobenzoate, vinyl tetrachlorobenzoate, vinyl naphthoate, and the like.

Examples of styrenes include styrene; alkylstyrenes such as methylstyrene, dimethylstyrene, trimethylstyrene, ethylstyrene, diethylstyrene, isopropylstyrene, butylstyrene, hexylstyrene, cyclohexylstyrene, decylstyrene, benzylstyrene, chloromethylstyrene, trifluoromethylstyrene, ethoxymethylstyrene, and acetoxymethylstyrene; alkoxystyrenes such as methoxystyrene, 4-methoxy-3-methylstyrene, and dimethoxystyrene; halostyrenes such as chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene, and 4-fluoro-3-trifluoromethylstyrene; and the like.

The molecular weight of the polymer having an epoxy group described above is not particularly limited as long as the object of the present invention is not impaired. The molecular weight of the polymer having an epoxy group is preferably 3,000 or more and 30,000 or less, and more preferably 5,000 or more and 15,000 or less, in terms of a polystyrene-equivalent weight average molecular weight.

The content of the (A) epoxy compound in the curable composition is appropriately determined in consideration of the epoxy equivalent of the (A) epoxy compound or the use amount of the (B) curing agent and preferable viscosity when the curable composition is used. The content of the (A) epoxy compound in the curable composition is typically, for example, 10% by mass or more and 95% by mass or less, preferably 20% by mass or more and 90% by mass or less, more preferably 30% by mass or more and 80% by mass or less, and further preferably 40% by mass or more and 70% by mass or less, with respect to the total mass of the component other than the solvent in the curable composition.

<Other Components>

The curable composition can contain additives such as a surfactant, a thermal polymerization inhibitor, an anti-foaming agent, a silane coupling agent, a coloring agent (pigment, dyestuff), resin (thermoplastic resin, alkali soluble resin, and the like), inorganic filler, and organic filler, if necessary. Conventionally known additives can be used for all the additives. Examples of the surfactant include an anionic compound, a cationic compound, and a non-ionic compound; examples of the thermal polymerization inhibitor include hydroquinone and hydroquinone monoethyl ether; and examples of the anti-foaming agent include a silicone-based compound and a fluorine-based compound.

The curable composition preferably contains a solvent in order to improve the coating properties thereof and to adjust the viscosity thereof. As the solvent, an organic solvent is typically used. Types of the organic solvent are not particularly limited as long as it can uniformly dissolve and disperse components included in the curable composition.

Suitable examples of the organic solvent that can be used as the solvent include (poly)alkyleneglycol monoalkylethers such as ethyleneglycol monomethylether, ethyleneglycol monoethylether, ethyleneglycol mono-n-propylether, ethyleneglycol mono-n-butylether, diethyleneglycol monomethylether, diethyleneglycol monoethylether, diethyleneglycol mono-n-propylether, diethyleneglycol mono-n-butylether, triethyleneglycol monomethylether, triethyleneglycol monoethylether, propyleneglycol monomethylether, propyleneglycol monoethylether, propyleneglycol mono-n-propylether, propyleneglycol mono-n-butylether, dipropyleneglycol monomethylether, dipropyleneglycol monoethylether, dipropyleneglycol mono-n-propylether, dipropyleneglycol mono-n-butylether, tripropyleneglycol monomethylether, and tripropyleneglycol monoethylether; (poly)alkyleneglycol monoalkylether acetates such as ethyleneglycol monomethylether acetate, ethyleneglycol monoethylether acetate, diethyleneglycol monomethylether acetate, diethyleneglycol monoethylether acetate, propyleneglycol monomethylether acetate, and propyleneglycol monoethylether acetate; other ethers such as diethyleneglycol dimethylether, diethyleneglycol methylethylether, diethyleneglycol diethylether, and tetrahydrofuran; ketones such as methylethylketone, cyclohexanone, 2-heptanone, and 3-heptanone; lactid acid alkyl esters such as methyl 2-hydroxypropionate, and ethyl 2-hydroxyprpionate; other esters such as ethyl 2-hydroxy-2-methylpropionate, methyl 3-methoxypropionate, ethyl 3-methoxypropionate, methyl 3-ethoxypropionate, ethyl 3-ethoxypropionate, ethyl ethoxyacetate, ethyl hydroxyacetate, methyl 2-hydroxy-3-methylbutanoate, 3-methyl-3-methoxybutyl acetate, 3-methyl-3-methoxybutyl propionate, ethyl acetate, n-propyl acetate, isopropyl acetate, n-butyl acetate, isobutyl acetate, n-pentyl formate, isopentyl acetate, n-butyl propionate, ethyl butanoate, n-propyl butanoate, isopropyl butanoate, n-butyl butanoate, methyl pyruvate, ethyl pyruvate, n-propyl pyruvate, methyl acetoacetate, ethyl acetoacetate, and ethyl 2-oxobutanoate; aromatic hydrocarbons such as toluene and xylene, and amides such as N-methylpyrrolidone, N,N-dimethylformamide, and N,N-dimethylacetamide. These organic solvents can be used independently, or by combining two or more types.

The use amount of the solvent in the curable composition is not particularly limited. From the viewpoint of coating characteristics of the curable composition, and the like, the use amount of the solvent is, for example, preferably 30% by mass or more and 99.9% by mass or less, and more preferably 50% by mass or more and 98% by mass or less with respect to the total of the curable composition. Furthermore, the viscosity of the curable composition is preferably adjusted to a range of 300 mPa·s or less. The viscosity of the curable composition is preferably 60 mPa·s or less, particularly preferably 30 mPa·s or less. The lower limit of the viscosity is not particularly limited, but it is 0.1 mPa·s or more. Note here that the above-mentioned viscosity is a viscosity measured at 25° C. using an E-type viscometer.

<<Method for Producing Curable Compositions>>

A curable composition can be produced by uniformly mixing respective components described above at a predetermined ratio. As a mixer which can be used for producing the curable composition, a two-roll or a three-roll can be exemplified. In a case where the viscosity of the curable composition is sufficiently low, in order to remove insoluble foreign matters, the curable composition may be filtered using a filter having an opening with a desired size if necessary.

<<Method for Producing Cured Product>>

A method for producing a cured product using the above-described curable composition is not particularly limited. Typically, a cured product is produced by a method including: molding the curable composition into a predetermined shape; and heating the molded curable composition.

A method for molding the curable composition is not particularly limited, but examples thereof include coating, and casting into a mold having a desired shape, and the like. Temperature and time for curing a curable composition which has been molded into a desired shape are not particularly limited as long as curing is sufficiently progressed. Specifically, for example, a curable composition can be cured by heating at a temperature of about 100° C. or more and 250° C. or less (preferably, 100° C. or more and 160° C. or less) for about one minute or more and 60 minutes or less (preferably 3 minutes or more and 10 minutes or less).

<<A Method for Producing Aromatic Amine Compound>>

A method for producing an aromatic amine compound represented by the above-described formula (a1) is not particularly limited. The method for producing an aromatic amine compound represented by the above-described formula (a1) can be produced by, for example, by hydrogenating a nitro group ($-NO_2$) of an aromatic nitro compound represented by the following formula (a1-1) to be converted into an amino group ($-NH_2$).

[Chem. 25]

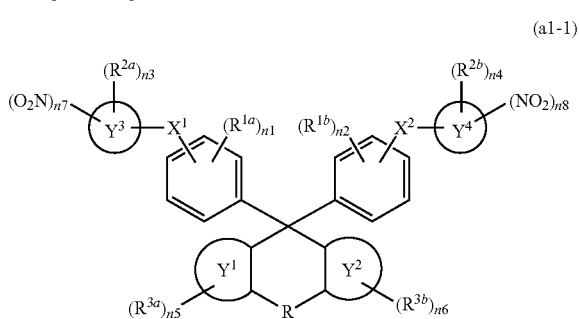

(a1-1)

wherein, in the formula (a1-1), $R^{1a}$, $R^{1b}$, $R^{2a}$, $R^{2b}$, $R^{3a}$, $R^{3b}$, $X^1$, $X^2$, a ring $Y^1$, a ring $Y^2$, a ring $Y^3$, a ring $Y^4$, R, and n1 to n8 are the same as those in the formula (a1).

The compound represented by the above formula (a1-1) is preferably a compound represented by the following formula (a1-1-1):

[Chem. 26]

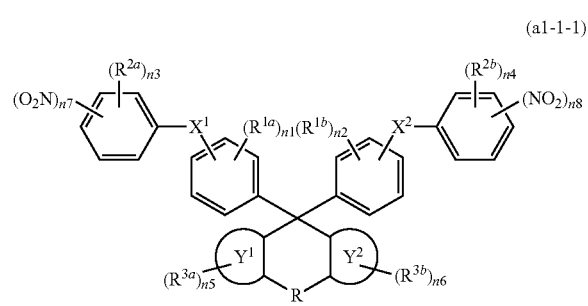

(a1-1-1)

wherein, in the formula (a1-1-1), $R^{1a}$, $R^{1b}$, $R^{2a}$, $R^{2b}$, $R^{3a}$, $R^{3b}$, $X^1$, $X^2$, a ring $Y^1$, a ring $Y^2$, R, and n1 to n8 are the same as those in the formula (a1).

A method for producing the compound represented by the formula (a1-1) is not particularly limited. For example, the compound represented by the formula (a1-1) can be produced by reacting an aromatic compound represented by the following formula (a1-1a), a compound represented by the following formula (a1-1b), a compound represented by the following formula (a1-1c):

[Chem. 27]

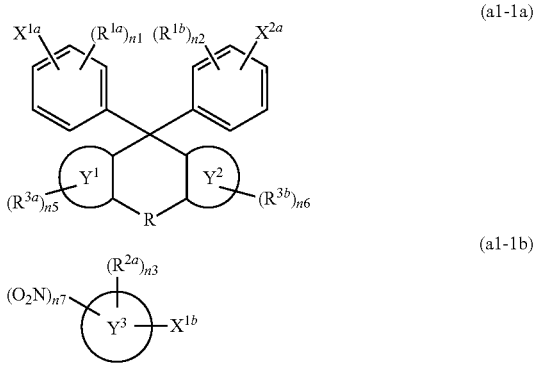

(a1-1a)

(a1-1b)

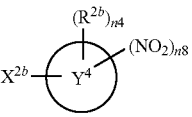

(a1-1c)

wherein, in the formulae (a1-1a), (a1-1b), and (a1-1c), $R^{1a}$, $R^{1b}$, $R^{2a}$, $R^{2b}$, $R^{3a}$, $R^{3b}$, a ring $Y^1$, a ring $Y^2$, a ring $Y^3$, a ring $Y^4$, R, and n1 to n8 are the same as those in the formula (a1); the group $X^{1a}$ is a group that forms a group $X^1$ in the formula (a1-1) by reaction with the group $X^{1b}$; and the group $X^{2a}$ is a group that forms a group $X^2$ in the formula (a1-1) by reaction with the group $X^{2b}$.

The reaction between the group $X^{1a}$ and the group $X^{1b}$ generates the group $X^1$, and the reaction between the group $X^{2a}$ and the group $X^{2b}$ generates the group $X^2$.

A combination of the group $X^{1a}$ and the group $X^{1b}$, and a combination of the group $X^{2a}$ and the group $X^{2b}$ are each independently
a combination of a carboxy group (—COOH) or a halocarbonyl group (—COHal) and an amino group (—NH$_2$),
a combination of a carboxy group (—COOH) or a halocarbonyl group (—COHal), and a hydroxyl group,
a combination of an amino group (—NH$_2$) and an isocyanate group,
a combination of a carboxy group (—COOH) or a halocarbonyl group (—COHal) and a carbamoyl group (—CO—NH$_2$),
a combination of hydroxyl group and an isocyanate group, or
a combination of a carbamoyl group (—CO—NH$_2$) and an isocyanate group. As to these combinations, for example, when the combination of the group $X^{1a}$ and the group $X^{1b}$ is a combination of a carboxy group and an amino group, $X^{1a}$ may be a carboxy group and $X^{1b}$ may be an amino group, and $X^{1a}$ may be an amino group and $X^{1b}$ may be a carboxy group.

The combination of a carboxy group (—COOH) or a halocarbonyl group (—COHal) and an amino group (—NH$_2$) is a combination to generate —CO—NH—. The combination of a carboxy group (—COOH) or a halocarbonyl group (—COHal), and a hydroxyl group is a combination to generate —CO—O—. The combination of an amino group (—NH$_2$) and an isocyanate group is a combination to generate —NH—CO—NH—. The combination of a carboxy group (—COOH) or a halocarbonyl group (—CO-Hal), and a carbamoyl group (—CO—NH$_2$) is a combination to generate —CO—NH—CO. The combination of a hydroxyl group and an isocyanate group is a combination to generate —O—CO—NH—. The combination of a carbamoyl group (—CO—NH$_2$) and an isocyanate group is a combination to generate —CO—NH—CO—NH—.

The method for reacting the aromatic compound represented by the formula (a1-1a), the compound represented by the following formula (a1-1b), and the compound represented by the following formula (a1-1c) is not particularly limited. The reaction method is appropriately selected from the well-known methods in view of the combination of group $X^{1a}$ and group $X^{1b}$, and the combination of the group $X^{2a}$ and the group $X^{2b}$.

The use amounts when the aromatic compound represented by the formula (a1-1a), the compound represented by the following formula (a1-1b), and the compound represented by the following formula (a1-1c) are reacted are not particularly limited as long as a desired amount of the compound represented by the formula (a1-1) can be generated. The use amount of the compound represented by the formula (a1-1b), and the use amount of the compound represented by the formula (a1-1c) are each independently particularly preferably 0.5 mol or more and 2 mol or less, more preferably 0.7 mol or more and 1.5 mol or less, and particularly preferably 0.9 mol or more and 1.1 mol or less relative to 1 mol of the compound represented by the formula (a1-1a).

A method for hydrogenating a nitro group ($-NO_2$) of an aromatic nitro compound represented by the formula (a1-1) to be converted into an amino group ($-NH_2$) is not particularly limited. The method can be appropriately selected from well-known hydrogenation methods for a nitro group. Typical examples of the methods include a method of bringing an aromatic nitro compound represented by the formula (a1-1) into contact with hydrogen in the presence of a palladium catalyst.

The aromatic amine compound can be produced by, for example, deprotecting an amino group that is protected by $Z^1$—NH— or $Z^2$—NH— of the aromatic compound of the following formula (a1-2) to be converted into an amino group ($-NH_2$).

[Chem. 28]

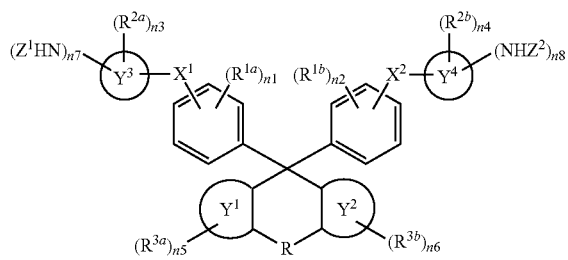

(a1-2)

(wherein, in the formula (a1-2), $R^{1a}$, $R^{1b}$, $R^{2a}$, $R^{2b}$, $R^{3a}$, $R^{3b}$, $X^1$, $X^2$, a ring $Y^1$, a ring $Y^2$, a ring $Y^3$, a ring $Y^4$, R, and n1 to n8 are the same as those in the formula (a1), $Z^1$ and $Z^2$ are each independently a protecting group capable of protecting and deprotecting an amino group).

As the compound represented by the formula (a1-2), the compound represented by the following formula (a1-1-1):

[Chem. 29]

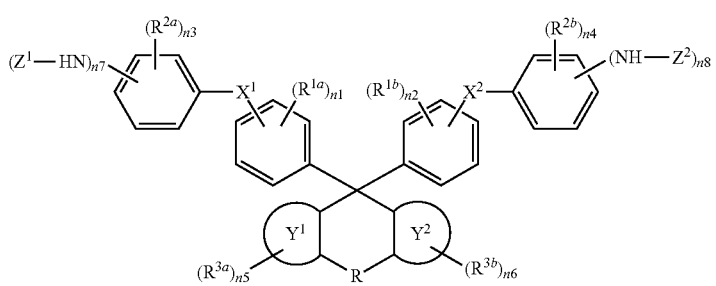

(a1-2-1)

(wherein, in the formula (a1-2-1), $R^{1a}$, $R^{1b}$, $R^{2a}$, $R^{2b}$, $R^{3a}$, $R^{3b}$, $X^1$, $X^2$, a ring $Y^1$, a ring $Y^2$, R, and n1 to n8 are the same as those in the formula (a1), $Z^1$ and $Z^2$ are each independently a protecting group capable of protecting and deprotecting an amino group) is preferable.

The protecting group as $Z^1$ and $Z^2$ are a functional group for converting an amino group into a different chemical group being substantially inactive to specific chemical reaction conditions. The protecting group can be easily and selectively removed at a preferable yield. Examples of the protecting group include a formyl group, an acetyl group, a benzyl group, a tert-butyldimethylsilyl group, a tert-butyldiphenylsilyl group, a tert-butyloxycarbonyl group (Boc), a p-methoxybenzyl group, a methoxymethyl group, a tosyl group, a trifluoroacetyl group, a trimethylsilyl (TMS) group, a fluorenylmethyloxycarbonyl group (Fmoc), a 2-trimethylsilylethoxycarbonyl group, a 1-methyl-1-(4-biphenylyl) ethoxycarbonyl group, an allyloxycarbonyl group, a benzyloxycarbonyl group (CBZ), a 2-trimethylsilylethanesulfonyl (SES), trityl and substituted trityl groups, a 9-fluorenylmethyloxy carbonyl group (FMOC), a nitro veratryloxycarbonyl (NVOC), and the like, but protecting groups are not limited thereto.

The method for producing a compound represented by the formula (a1-2) is not particularly limited. For example, the compound represented by the formula (a1-2) can be produced by reacting the aromatic compound represented by the following formula (a1-1a), the compound represented by the following formula (a1-2b), and the compound represented by the following formula (a1-2c):

[Chem. 30]

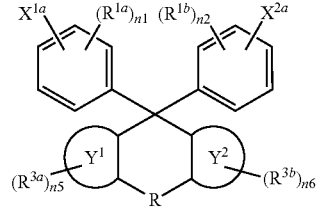

(a1-1a)

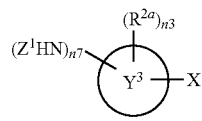

(a1-2b)

-continued

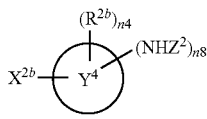
(a1-2c)

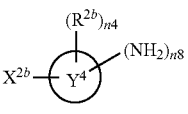
(a1-3c)

(wherein, in the formulae (a1-1a), (a1-2b), and (a1-2c), $R^{1a}$, $R^{1b}$, $R^{2a}$, $R^{2b}$, $R^{3a}$, $R^{3b}$, a ring $Y^1$, a ring $Y^2$, a ring $Y^3$, a ring $Y^4$, R, and n1 to n8 are the same as those in the formula (a1), and $Z^1$ and $Z^2$ are the same as those in the formula (a1-2);

a group $X^{1a}$ is a group that is reacted with a group $X^{1b}$ to form a group $X^1$ in the formula (a1-2), and a group $X^{2a}$ is a group that is reacted with a group $X^{2b}$ to form a group $X^2$ in the formula (a1-2).

A combination of the group $X^{1a}$ and the group $X^{1b}$, and a combination of the group $X^{2a}$ and the group $X^{2b}$ are the same as those described in the reaction of the aromatic compound represented by the formula (a1-1a), the compound represented by the formula (a1-1b), and the compound represented by the formula (a1-1c).

The use amounts when the aromatic compound represented by the formula (a1-1a), the compound represented by the following formula (a1-2b), and the compound represented by the following formula (a1-2c) are reacted are not particularly limited as long as a desired amount of the compound represented by the formula (a1-2) can be generated. The use amount of the compound represented by the formula (a1-2b), and the use amount of the compound represented by the formula (a1-2c) are each independently particularly preferably 0.5 mol or more and 2 mol or less, more preferably 0.7 mol or more and 1.5 mol or less, and particularly preferably 0.9 mol or more and 1.1 mol or less relative to 1 mol of the compound represented by the formula (a1-1a).

A method for deprotecting the protected amino group represented by $Z^1$—NH— or $Z^2$—NH— to be converted into an amino group (—NH$_2$) is not particular limited as long as the method is conventionally known methods. Deprotection is carried out by the well-known means according to types of the protecting group.

Furthermore, the aromatic amine compound represented by the formula (a1) can be produced by reacting the compound represented by the following formula (a1-3b), the compound represented by the following formula (a1-3c), and the following aromatic compound represented by the formula (a1-1a):

[Chem. 31]

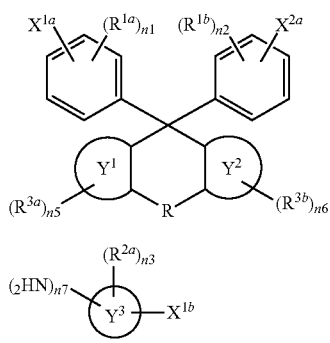

(a1-1a)

(a1-3b)

(wherein in the formula (a1-1a), the formula (a1-1b), and the formula (a1-1c), $R^{1a}$, $R^{1b}$, $R^{2a}$, $R^{2b}$, $R^{3a}$, $R^{3b}$, a ring $Y^1$, a ring $Y^2$, a ring $Y^3$, a ring $Y^4$, R, and n1 to n8 are the same as those in the formula (a1), a group $X^{1a}$ is a group that forms a group $X^1$ in the formula (a1) by a reaction with a group $X^{1b}$, and a group $X^{2a}$ is a group that forms a group $X^2$ in the formula (a1)) by a reaction with a group $X^{2b}$. Since this method does not need hydrogenation of a nitro group and deprotection of the protected amino group, which may cause side reaction, the synthesis of the aromatic amine compound represented by the formula (a1) is easy.

A combination of the group $X^{1a}$ and the group $X^{1b}$, and a combination of the group $X^{2a}$ and the group $X^{2b}$ are the same as those described in the reaction of the aromatic compound represented by the formula (a1-1a), the compound represented by the formula (a1-1b), and the compound represented by the formula (a1-1c). However, when the aromatic compound represented by the formula (a1-1a), the compound represented by the formula (a1-3b), and the compound represented by the formula (a1-3c) are reacted, the combination of the group $X^{1a}$ and the group $X^{1b}$ and the combination of the group $X^{2a}$ and the group $X^{2b}$ are limited to a combination of a carboxy group (—COOH) or a halocarbonyl group (—COHal) and an amino group (—NH$_2$), a combination of a carboxy group (—COOH) or a halocarbonyl group (—COHal), and a hydroxyl group, or a carboxy group (—COOH) or a halocarbonyl group (—COHal) and a carbamoyl group (—CO—NH$_2$).

EXAMPLES

Hereinafter, the present invention will be described more specifically with reference to Examples. Note here that the scope of the present invention is not limited to the scope of Examples.

Example 1

In a four neck flask equipped with a thermometer, a dropping funnel, and a stirring blade, 2 mL of thionyl chloride was added to a pyridine solution of 4-aminobenzoic acid (2.74 g, 0.02 mol). After thionyl chloride was added, the content of the flask was stirred at room temperature for three hours to obtain 4-aminobenzoyl chloride. To the obtained 4-aminobenzoyl chloride, 9,9'-bis(4-aminophenyl)fluorene (3.48 g, 0.01 mol) dissolved in N-methyl-2-pyrrolidone (NMP) was added, and the obtained product was stirred for five hours. The obtained reaction solution was poured little by little into ice water at 0 to 5° C., stirred at a constant speed, followed by solid-liquid separation. In order to remove unreacted 4-aminobenzoic acid, the separated wet product was washed with a sodium hydrogen carbonate aqueous solution having a concentration of 10% by mass four times. Then, the wet product was washed with anhydrous methanol, and then dried at 80° C. to obtain 9,9'-bis(4-(4-aminobenzoylamino)phenyl)fluorene at the yield of 58%.

$^1$H-NMR measurement results of 9,9'-bis(4-(4-aminobenzoylamino)phenyl)fluorene are as follows.

$^1$H-NMR (400 MHz, DMSO-d6) δ=9.72 (2H, s), 7.94 (2H, d), 7.70 (4H, d), 7.65 (4H, d), 7.3-7.5 (6H, m)

Example 2

To a four neck flask equipped with a thermometer, a dropping funnel, and a stirring blade, an NMP solution of 9,9'-bis(4-aminophenyl)fluorene (3.48 g, 0.01 mol) was added. Internal temperature of the flask was raised to 60° C., and then a mixture solution of 4-nitrobenzoyl chloride (3.72 g, 0.02 mol) and 9.2 g of toluene was dropped into a can. The solution in the flask was stirred at the same temperature for 2 hours, and then 50 g of methanol was dropped into a flask. The obtained reaction solution was poured little by little into ice water at 0 to 5° C., stirred at constant a speed, followed by solid-liquid separation to obtain 3.23 g of 9,9'-bis(4-(4-nitrobenzamide)phenyl)fluorene (yield: 50%).

Subsequently, into a 100-mL autoclave, the obtained 9,9'-bis(4-(4-nitrobenzamide)phenyl)fluorene (3.23 g, 0.005 mol), 10 g of tetrahydrofuran, 3 g of NMP, 0.8 g of n-butylamine, 0.2 g of 5% Pd/C were charged. Then, hydrogenation reaction was carried out under the conditions in which the temperature inside the can was 20 to 30° C., and hydrogen pressure was 0 to 0.05 MPa(G). From the time when hydrogen absorption was completed, the temperature of the reaction solution was maintained at 35 to 40° C. for 2 hours to complete the catalytic hydrogenation reaction. After reaction, using a membrane filter, catalytic filtration was carried out to obtain a filtrate. To the filtrate, 0.7 g of acetic acid and 20 g of methanol were charged, and then, 20 g of ion exchanged water was dropped. Then, the temperature inside the can was decreased to 10° C., and solid-liquid separation was carried out to obtain a wet product. The obtained wet product was dried to obtain 3.00 g of 9,9'-bis (4-(4-aminobenzoylamino)phenyl)fluorene.

According to Example 2, it was verified that 9,9'-bis(4-(4-aminobenzoylamino)phenyl)fluorene as the aromatic amine compound represented by the formula (a1) was produced from the compound represented by the formula (a1-2b), the compound represented by the formula (a1-2c), and the aromatic compound represented by the formula (a1-1a).

Example 3

In the same manner as in Example 1 except that 4-aminobenzoic acid was changed to 3-aminobenzoic acid, 9,9'-bis(4-(3-aminobenzoylamino)phenyl)fluorene was obtained at the yield of 47%.

Example 4

In the same manner as in Example 2 except that 4-nitrobenzoic acid was changed to 3-nitrobenzoic acid, 2.78 g of 9,9'-bis(4-(3-aminobenzoylamino)phenyl)fluorene was obtained.

Examples 5 to 10, and Comparative Examples 1 to 4

(A) epoxy compounds and (B) curing agents in the amounts respectively described in Table 1 were mixed to obtain curable compositions of Examples and Comparative Examples. Note here that in Comparative Example 1, no (B) curing agent components were used. Furthermore, in Examples 7 to 10 and Comparative Examples 3 and 4, propylene glycol monomethyl ether was further added to adjust the solid content concentration of the curable composition to 25% by mass. In Example 5 and Comparative Examples 1 and 2, as the (A) epoxy compound, bisphenol A diglycidylether (bisphenol A type epoxy resin, Ep-1) was used. In Examples 6 to 10 and Comparative Examples 3 and 4, as the (A) epoxy compound described below, the following Ep-2 to Ep-6 were used, respectively. Ep-6 is a resin composed of constituent units having structures shown in parentheses. In the following formula for Ep-6, a number given in a lower right of each parenthesis shows the mass ratio (% by mass) of each constituent unit in the resin.

[Chem. 32]

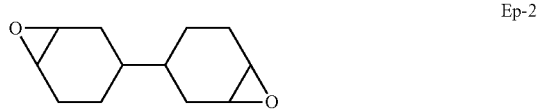
Ep-2

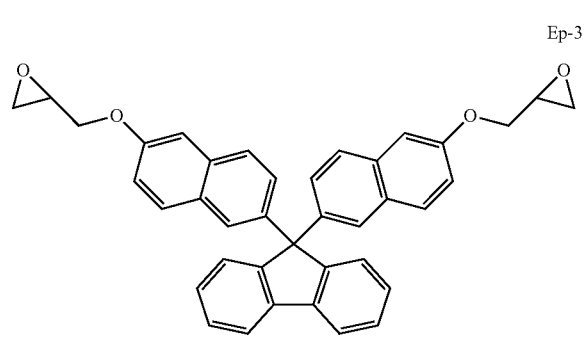
Ep-3

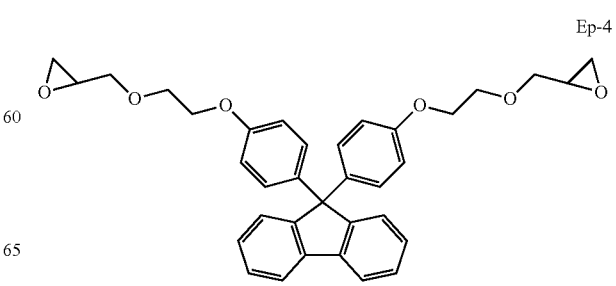
Ep-4

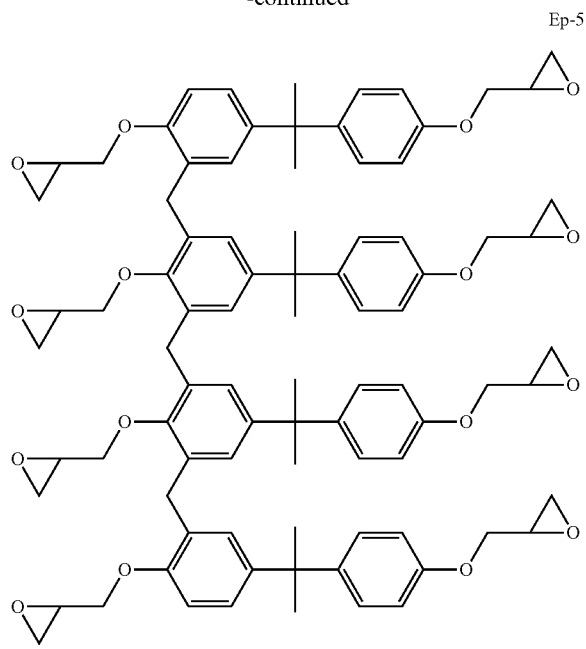

Ep-5

Ep-6

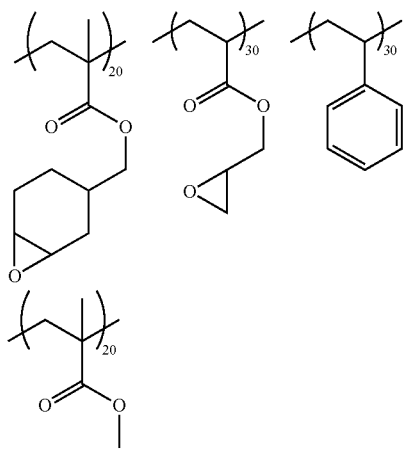

In Examples 5 to 10, 9, 9'-bis(4-(4-aminobenzoylamino)phenyl)fluorene obtained in Example 1 was used as the curing agent 1. In Comparative Example 2, 1-methyl imidazole was used as the curing agent 2.

<Evaluation of Curability>

A curable composition was injected into space having a width of 2 mm which was formed between two molds. The curable composition injected into the space was heated for 5 minutes, and then the molds were removed to obtain a plate-like test piece having a thickness of 2 mm. It was checked whether or not a test piece reached a tack-free state in which a surface of the test piece was free from tackiness, which was used as a guide of curing. The curability was evaluated according to the following criteria.

⊚: Test piece was cured at heating temperature of 130° C. or lower.

○: Test piece was cured at heating temperature of higher than 130° C. and 160° C. or lower.

x: Test piece was not cured at heating temperature of higher than 130° C. and 160° C. or lower.

<Evaluation of Bottle Stability>

The viscosity (cP) immediately after the curable composition was prepared was measured using an E type viscometer (TV-20 type, cone-plate type, manufactured by Toki Sangyo Co., Ltd.). Furthermore, the viscosity of the curable composition was measured after the curable composition was stored at 25° C. The bottle stability was evaluated according to the following criteria.

⊚: The viscosity after the storage for 30 days was increased from the initial viscosity by less than 20 cP.

○: The viscosity after the storage for 10 days was increased from the initial viscosity by less than 20 cP, but the viscosity after the storage for 30 days was increased from the initial viscosity by 20 cP or more.

x: The viscosity after the storage for 10 days was increased from the initial viscosity by 20 cP or more.

TABLE 1

| | Epoxy compound | | Curing agent1 | Curing agent2 | Low temperature curability | Bottle stability |
|---|---|---|---|---|---|---|
| | Type | (Part by mass) | (Part by mass) | (Part by mass) | | |
| Example5 | Ep-1 | 95 | 5 | — | ⊚ | ⊚ |
| Example6 | Ep-2 | 95 | 5 | — | ⊚ | ⊚ |
| Example7 | Ep-3 | 95 | 5 | — | ⊚ | ⊚ |
| Example8 | Ep-4 | 95 | 5 | — | ⊚ | ⊚ |
| Example9 | Ep-5 | 95 | 5 | — | ⊚ | ⊚ |
| Example10 | Ep-6 | 95 | 5 | — | ⊚ | ⊚ |
| Comparative Example1 | Ep-1 | 100 | — | — | ○ | ⊚ |
| Comparative Example2 | Ep-1 | 95 | — | 5 | ○ | X |
| Comparative Example3 | Ep-3 | 100 | — | — | X | ⊚ |
| Comparative Example4 | Ep-4 | 100 | — | — | X | ⊚ |

Table 1 shows that the aromatic amine compound represented by the formula (a1) satisfactorily cures an epoxy compound, and a curable composition including the aromatic amine compound represented by the formula (a1) as a curing agent is excellent in the bottle stability.

In the curable composition of Comparative Example 1 including Ep-1 as the epoxy compound (A) and not including a curing agent, curing proceeded to a tack-free state although slightly high temperature was required. On the other hand, curable compositions of Comparative Examples 3 and 4, including Ep-3 and Ep-4 as the epoxy compound (A), respectively, and not including a cuing agent, were not cured even at a temperature of higher than 160° C. However, the curable compositions of Examples 7 and 8 including Ep-3 and Ep-4 as the epoxy compound (A) together with the aromatic amine compound represented by the formula (a1) was satisfactorily cured even at a low temperature of 130° C. or lower. From the comparison between Example 5 and Comparative Example 1, apparently it may be understood that a curing acceleration effect of the aromatic amine compound represented by the formula (a1) on the epoxy compound is not remarkable. However, according to the comparison between Examples 7 and 8, and Comparative Examples 3 and 4, it is shown that the curing acceleration effect of the aromatic amine compound represented by the formula (a1) on the epoxy compound is remarkable.

The invention claimed is:

1. An aromatic amine compound represented by the following formula (a1):

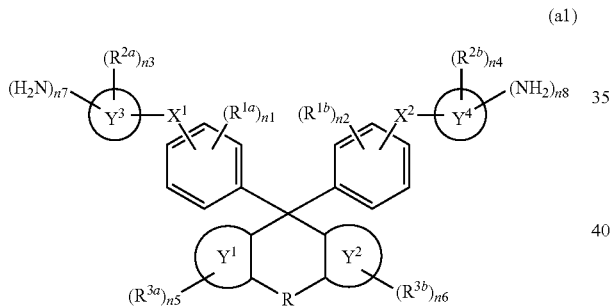

(a1)

wherein, in the formula (a1), $R^{1a}$, $R^{1b}$, $R^{2a}$, $R^{2b}$, $R^{3a}$, and $R^{3b}$ are each independently a monovalent hydrocarbon group, a group represented by —$OR^{4a}$, a group represented by —$SR^{4b}$, an acyl group, an alkoxycarbonyl group, a halogen atom, a cyano group, a group represented by —$NHR^{4c}$, or a group represented by —$N(R^{4d})_2$, wherein the monovalent hydrocarbon group, the group represented by —$OR^{4a}$, the group represented by —$SR^{4b}$, the acyl group, the alkoxycarbonyl group, the group represented by —$NHR^{4c}$, and the group represented by —$N(R^{4d})_2$ may be substituted by one or more groups selected from the group consisting of a group represented by —$OR^{4e}$, a group represented by —$SR^{4f}$, an acyl group, an alkoxycarbonyl group, a halogen atom, a cyano group, and a group represented by —$NHR^{4g}$;

$R^{4a}$ to $R^{4g}$ are each independently a monovalent hydrocarbon group;

$X^1$ and $X^2$ are each independently —CO—NH—, —CO—NH—CO—, —O—CO—NH—, or —CO—NH—CO—NH—;

a ring $Y^1$, a ring $Y^2$, a ring $Y^3$, and a ring $Y^4$ each independently represent an aromatic hydrocarbon ring;

R is a single bond, a methylene group which may have a substituent, an ethylene group which may have a substituent and including a heteroatom between two carbon atoms, a group represented by —O—, a group represented by —NH—, or a group represented by —S—;

n1 and n2 are each independently an integer of 0 or more and 4 or less;

n3 and n4 are each independently an integer of 0 or more and 5 or less;

n5 and n6 are each independently an integer of 0 or more and 4 or less;

n7 and n8 are each independently an integer of 0 or more and 2 or less;

n3+n7 and n4+n8 are each independently an integer of 0 or more and 5 or less; and n7+n8 is an integer of 1 or more and 4 or less.

2. The aromatic amine compound according to claim 1, wherein said compound is represented by the following formula (a2):

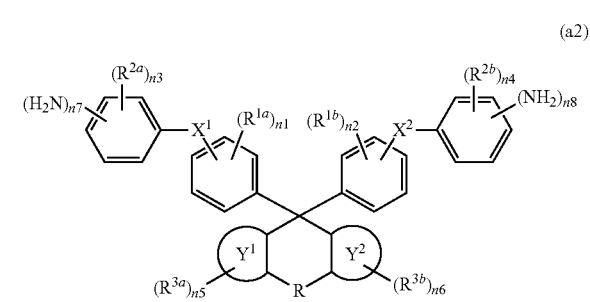

(a2)

wherein in the formula (a2), $R^{1a}$, $R^{1b}$, $R^{2a}$, $R^{2b}$, $R^{3a}$, $R^{3b}$, $X^1$, $X^2$, a ring $Y^1$, a ring $Y^2$, R, and n1 to n8 are the same as those in the formula (a1).

3. The aromatic amine compound according to claim 2, wherein said compound is represented by the following formula (a3):

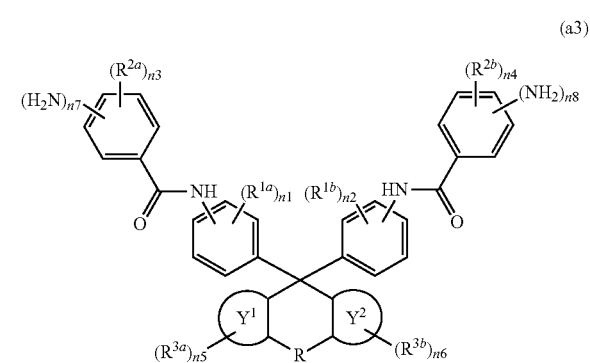

(a3)

wherein, in the formula (a3), $R^{1a}$, $R^{1b}$, $R^{2a}$, $R^{2b}$, $R^{3a}$, $R^{3b}$, a ring $Y^1$, a ring $Y^2$, R, and n1 to n8 are the same as those in the formula (a1).

4. The aromatic amine compound according to claim 3, wherein said compound is represented by the following formula (a4):

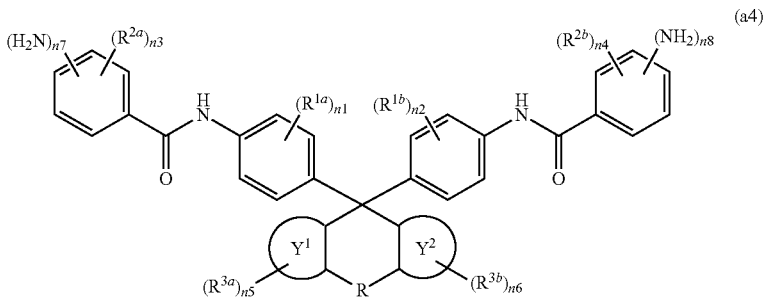

(a4)

wherein, in the formula (a4), $R^{1a}$, $R^{1b}$, $R^{2a}$, $R^{2b}$, $R^{3a}$, $R^{3b}$, a ring $Y^1$, a ring $Y^2$, R, and n1 to n8 are the same as those in the formula (a1).

5. The aromatic amine compound according to claim 3, wherein said compound is represented by the following formula (a5):

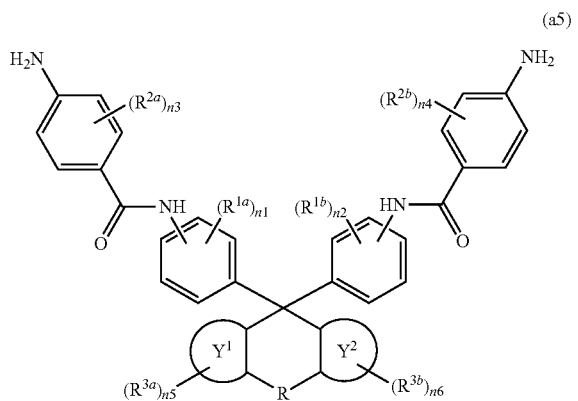

(a5)

wherein, in the formula (a5), $R^{1a}$, $R^{1b}$, $R^{2a}$, $R^{2b}$, $R^{3a}$, $R^{3b}$, a ring $Y^1$, a ring $Y^2$, R, and n1 to n6 are the same as those in the formula (a1).

6. The aromatic amine compound according to claim 4, wherein said compound is represented by the following formula (a6):

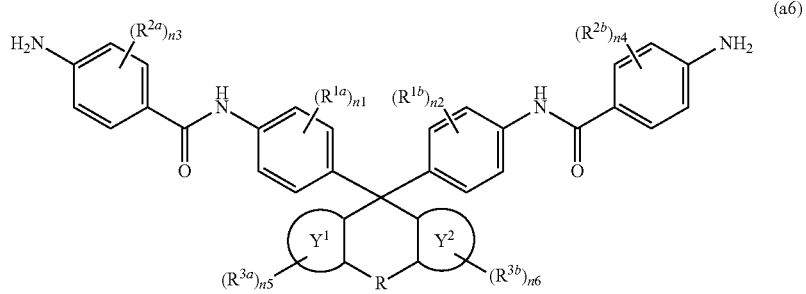

(a6)

wherein, in the formula (a6), $R^{1a}$, $R^{1b}$, $R^{2a}$, $R^2$, $R^{3a}$, $R^{3b}$, a ring $Y^1$, a ring $Y^2$, R, and n1 to n6 are the same as those in the formula (a1).

7. The aromatic amine compound according to claim 1, wherein the ring $Y^1$ and the ring $Y^2$, are each independently a benzene ring, and the R is a single bond.

8. A curing agent for an epoxy compound, comprising the aromatic amine compound according to claim 1.

9. A curable composition comprising an (A) epoxy compound and a (B) curing agent, wherein the (B) curing agent is the curing agent for an epoxy compound according to claim 8.

10. A method for producing a cured product, the method comprising:
    molding the curable composition according to claim 9 into a predetermined shape; and
    heating the molded curable composition.

11. A method for producing an aromatic amine compound according to claim 1, the method comprising hydrogenating a nitro group of an aromatic nitro compound represented by the following formula (a1-1):

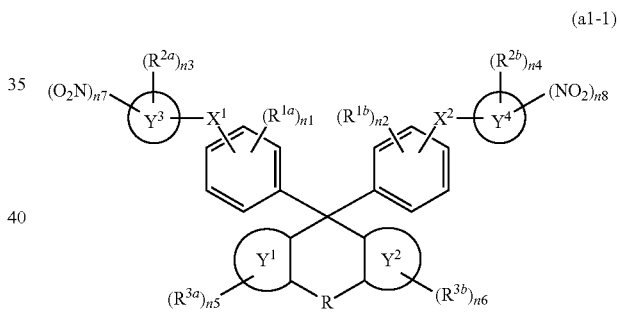

(a1-1)

wherein, in the formula (a1-1), $R^{1a}$, $R^{1b}$, $R^{2a}$, $R^{2b}$, $R^{3a}$, $R^{3b}$, $X^1$, $X^2$, a ring $Y^1$, a ring $Y^2$, a ring $Y^3$, a ring $Y^4$, R, and n1 to n8 are the same as those in the formula (a1), to be converted into an amino group.

12. The method according to claim 11, further comprising reacting an aromatic compound represented by the following formula (a1-1a), a compound represented by the following formula (a1-1b), and a compound represented by the following formula (a1-1c):

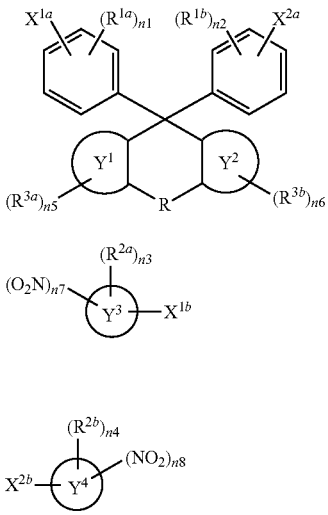

(a1-1a)

(a1-1b)

(a1-1c)

wherein, in the formulae (a1-1a), (a1-1b), and (a1-1c), $R^{1a}$, $R^{1b}$, $R^{2a}$, $R^{2b}$, $R^{3a}$, $R^{3b}$, a ring $Y^1$, a ring $Y^2$, a ring $Y^3$, a ring $Y^4$, R, and n1 to n8 are the same as those in the formula (a1), a group $X^{1a}$ is a group that is reacted with a group $X^{1b}$ to form a group $X^1$ in the formula (a1-1), and a group $X^{2a}$ is a group that forms a group $X^2$ in the formula (a1-1) by a reaction with a group $X^{2b}$, to produce the aromatic nitro compound represented by the formula (a1-1), wherein the group $X^{1a}$ and the group $X^{1b}$ are reacted with each other to produce the group $X^1$, and the group $X^{2a}$ and the group $X^{2b}$ are reacted with each other to produce the group $X^2$;

wherein a combination of the group $X^{1a}$ and the group $X^{1b}$, and a combination of the group $X^{2a}$ and the group $X^{2b}$ are each independently a combination of a carboxy group (—COOH) or a halocarbonyl group (—COHal) and an amino group (—NH$_2$), a combination of a carboxy group (—COOH) or a halocarbonyl group (—COHal) and a carbamoyl group (—CO—NH$_2$), a combination of hydroxyl group and an isocyanate group, or a combination of a carbamoyl group (—CO—NH$_2$) and an isocyanate group.

13. A method for producing an aromatic amine compound according to claim 1, the method comprising:

deprotecting an amino group that is protected by $Z^1$—NH— or $Z^2$—NH— of the aromatic compound represented by the following formula (a1-2):

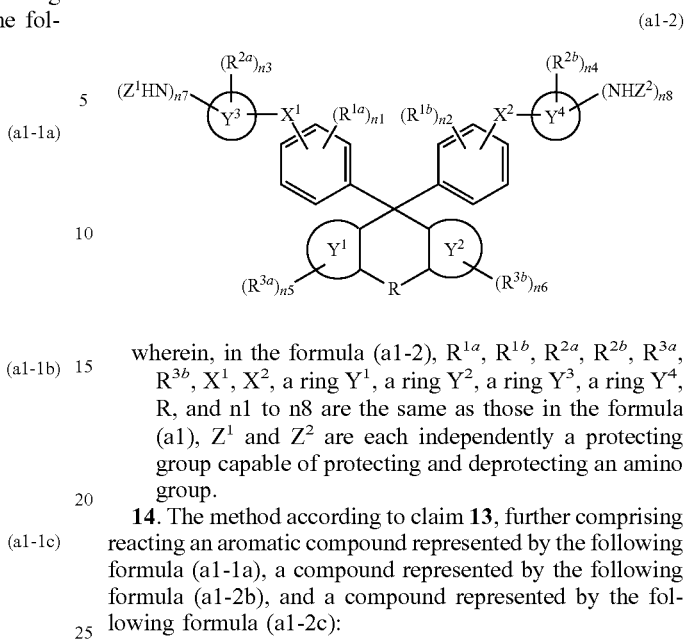

(a1-2)

wherein, in the formula (a1-2), $R^{1a}$, $R^{1b}$, $R^{2a}$, $R^{2b}$, $R^{3a}$, $R^{3b}$, $X^1$, $X^2$, a ring $Y^1$, a ring $Y^2$, a ring $Y^3$, a ring $Y^4$, R, and n1 to n8 are the same as those in the formula (a1), $Z^1$ and $Z^2$ are each independently a protecting group capable of protecting and deprotecting an amino group.

14. The method according to claim 13, further comprising reacting an aromatic compound represented by the following formula (a1-1a), a compound represented by the following formula (a1-2b), and a compound represented by the following formula (a1-2c):

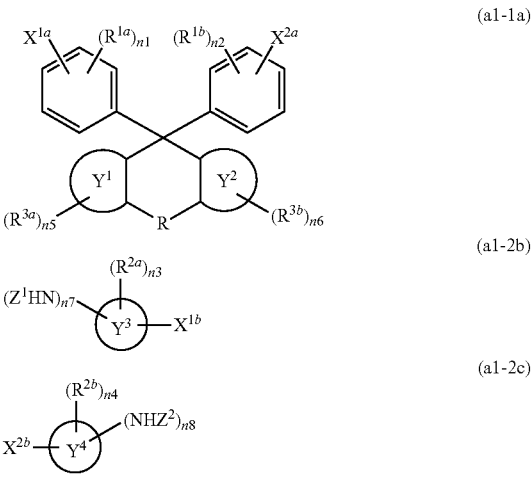

(a1-1a)

(a1-2b)

(a1-2c)

wherein, in the formulae (a1-1a), (a1-2b), and (a1-2c), $R^{1a}$, $R^{1b}$, $R^{2a}$, $R^{2b}$, $R^{3a}$, $R^{3b}$, a ring $Y^1$, a ring $Y^2$, a ring $Y^3$, a ring $Y^4$, R, and n1 to n8 are the same as those in the formula (a1), and $Z^1$ and $Z^2$ are the same as in the formula (a1-2), a group $X^{1a}$ is a group that forms a group $X^1$ in the formula (a1-2) by a reaction with a group $X^{1b}$, and a group $X^{2a}$ is a group that forms a group $X^2$ in the formula (a1-2) by a reaction with a group $X^{2b}$, to produce the aromatic compound represented by the formula (a1-2), wherein the reaction between the group $X^{1a}$ and the group $X^{1b}$ generates the group $X^1$, and the reaction between the group $X^{2a}$ and the group $X^{2b}$ generates the group $X^2$;

wherein a combination of the group $X^{1a}$ and the group $X^{1b}$ and a combination of the group $X^{2a}$ and the group $X^{2b}$ are each independently a combination of a carboxy group (—COOH) or a halocarbonyl group (—COHal) and an amino group (—NH$_2$), a combination of a carboxy group (—COOH) or a halocarbonyl group (—COHal) and a carbamoyl group (—CO—NH$_2$), a combination of hydroxyl group and an isocyanate group, or a combination of a carbamoyl group (—CO—NH$_2$) and an isocyanate group.

15. A method for producing an aromatic amine compound according to claim 1, the method comprising reacting an aromatic compound represented by the following formula (a1-1a), a compound represented by the following formula (a1-3b), and a compound represented by the following formula (a1-3c):

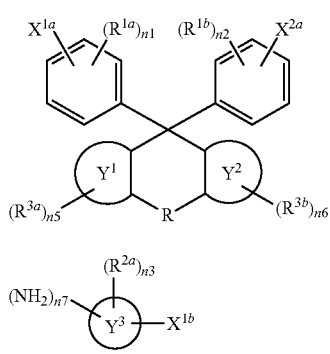

(a1-1a)

(a1-3b)

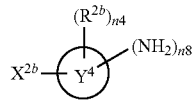

(a1-3c)

wherein, in the formulae (a1-1a), (a1-3b), and (a1-3c), $R^{1a}$, $R^{1b}$, $R^{2a}$, $R^{2b}$, $R^{3a}$, $R^{3b}$, a ring $Y^1$, a ring $Y^2$, a ring $Y^3$, a ring $Y^4$, R, and n1 to n8 are the same as those in the formula (a1), a group $X^{1a}$ is a group that forms a group $X^1$ in the formula (a1) by a reaction with a group $X^{1b}$, and a group $X^{2a}$ is a group that forms a group $X^2$ in the formula (a1) by a reaction with a group $X^{2b}$, to produce the aromatic amine compound represented by the formula (a1), wherein the reaction between the group $X^{1a}$ and the group $X^{1b}$ generates the group $X^1$, and the reaction between the group $X^{2a}$ and the group $X^{2b}$ generates the group $X^2$;

wherein a combination of the group $X^{1a}$ and the group $X^{2b}$ and a combination of the group $X^{2a}$ and the group $X^{2b}$ are each independently a combination of a carboxy group (—COOH) or a halocarbonyl group (—COHal) and an amino group (—NH$_2$), or a combination of a carboxy group (—COOH) or a halocarbonyl group (—COHal) and a carbamoyl group (—CO—NH$_2$).

* * * * *